US009504565B2

(12) United States Patent
Armstrong

(10) Patent No.: US 9,504,565 B2
(45) Date of Patent: Nov. 29, 2016

(54) ASYMMETRIC OPENING AND CLOSING PROSTHETIC VALVE LEAFLET

(71) Applicant: W. L. Gore & Associates, Inc., Newark, DE (US)

(72) Inventor: Joseph R. Armstrong, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 14/561,148

(22) Filed: Dec. 4, 2014

(65) Prior Publication Data

US 2015/0157456 A1 Jun. 11, 2015

Related U.S. Application Data

(60) Provisional application No. 61/974,653, filed on Apr. 3, 2014, provisional application No. 61/913,235, filed on Dec. 6, 2013.

(51) Int. Cl.
*A61F 2/24* (2006.01)

(52) U.S. Cl.
CPC ........... *A61F 2/2418* (2013.01); *A61F 2/2412* (2013.01); *A61F 2/2415* (2013.01); *A61F 2/24* (2013.01); *A61F 2210/0076* (2013.01); *A61F 2250/0014* (2013.01); *A61F 2250/0018* (2013.01); *A61F 2250/0029* (2013.01); *A61F 2250/0036* (2013.01); *Y10T 29/49901* (2015.01)

(58) Field of Classification Search
CPC ............... A61F 2250/0036; A61F 2250/0039; A61F 2250/0018; A61F 2/2412
USPC .......................................................... 623/24
See application file for complete search history.

(56) References Cited

U.S. PATENT DOCUMENTS

| 3,953,566 A | 4/1976 | Gore |
| 4,222,126 A | 9/1980 | Boretos et al. |
| 5,708,044 A | 1/1998 | Branca |
| 6,174,331 B1 * | 1/2001 | Moe ...................... A61F 2/2412 623/2.12 |

(Continued)

FOREIGN PATENT DOCUMENTS

| EP | 1 318 775 | 6/2003 |
| WO | 0224119 | 3/2002 |

OTHER PUBLICATIONS

International Search Report and Written Opinion for PCT/US2014/068727 mailed Mar. 2, 2015, corresponding to U.S. Appl. No. 14/561,148; 6 pages.

*Primary Examiner* — Jacqueline Woznicki

(57) ABSTRACT

Described embodiments are directed toward prosthetic valves having leaflets that move asymmetrically in that a leaflet second side region of the leaflet initially moves toward the open position before a leaflet first side region and the leaflet first side region initially moves toward the closed position before the leaflet second side region. In the fully open position, the leaflet first side region opens less than the leaflet second side region. Asymmetric opening and final open position, in synchrony with the other leaflets having the same motion and final open position creates spiral flow exiting the open valve that increases blood flow on the downstream side of the leaflet and thus reduces stagnation of the blood that might lead to thrombus formation. Controlled asymmetric movement of the leaflet reduces closing volume by initiating closure on the leaflet first side region and finishing closures on the leaflet second side region.

28 Claims, 14 Drawing Sheets

(56) References Cited

U.S. PATENT DOCUMENTS

| | | |
|---|---|---|
| 6,283,994 B1 | 9/2001 | Moe et al. |
| 6,541,589 B1 | 4/2003 | Baillie |
| 6,562,069 B2 * | 5/2003 | Cai ...................... A61F 2/2412 623/2.12 |
| 6,953,332 B1 * | 10/2005 | Kurk ..................... A61F 2/2415 249/52 |
| 7,306,729 B2 | 12/2007 | Bacino et al. |
| 7,462,675 B2 | 12/2008 | Chang et al. |
| 7,531,611 B2 | 5/2009 | Sabol et al. |
| 8,167,935 B2 | 5/2012 | McGuckin, Jr. et al. |
| 8,475,512 B2 * | 7/2013 | Hunt ..................... A61F 2/2412 623/1.1 |
| 8,637,144 B2 | 1/2014 | Ford |
| 2003/0055496 A1 * | 3/2003 | Cai ...................... A61F 2/2412 623/2.19 |
| 2003/0097175 A1 | 5/2003 | O'Connor et al. |
| 2003/0229394 A1 * | 12/2003 | Ogle ..................... A61F 2/2415 623/2.14 |
| 2004/0024448 A1 | 2/2004 | Chang et al. |
| 2006/0265053 A1 * | 11/2006 | Hunt ..................... A61F 2/2412 623/1.24 |
| 2010/0248324 A1 | 9/2010 | Xu et al. |
| 2012/0123530 A1 | 5/2012 | Carpentier et al. |
| 2012/0323315 A1 * | 12/2012 | Bruchman ............ A61F 2/2415 623/2.17 |
| 2013/0166021 A1 | 6/2013 | Bruchman et al. |
| 2014/0005773 A1 | 1/2014 | Wheatley |
| 2014/0163673 A1 * | 6/2014 | Bruchman ............. A61L 27/34 623/2.42 |

\* cited by examiner

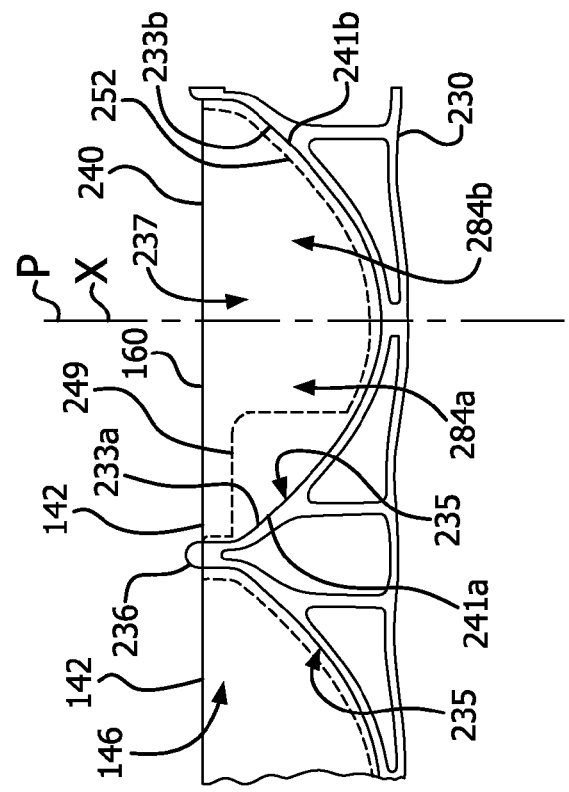
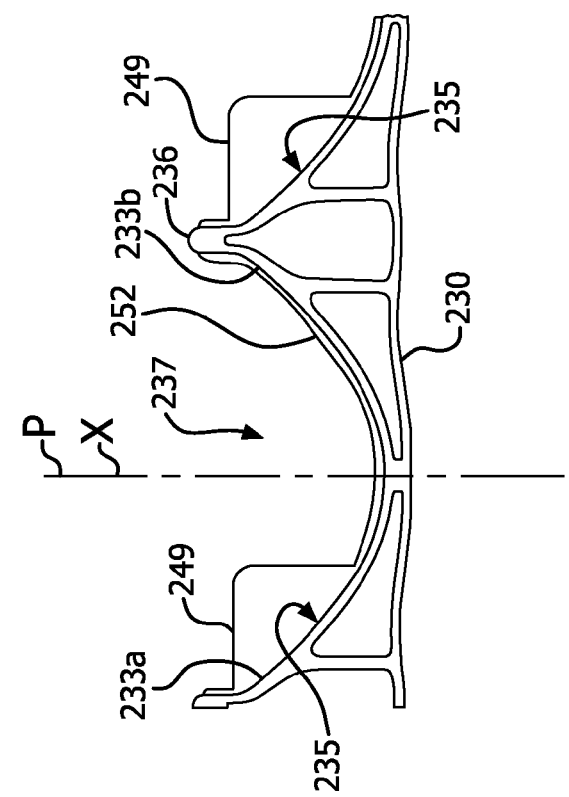

ASYMMETRIC OPENING AND CLOSING PROSTHETIC VALVE LEAFLET

FIELD

The present disclosure relates generally to prosthetic valves and more specifically, synthetic flexible leaflet-type prosthetic valve devices and methods.

BACKGROUND

Bioprosthetic valves have been developed that attempt to mimic the function and performance of a native valve. Flexible leaflets are fabricated from biological tissue such as bovine pericardium. In some valve designs the biological tissue is sewn onto a relatively rigid frame that supports the leaflets and provides dimensional stability when implanted. Although bioprosthetic valves can provide excellent hemodynamic and biomechanical performance in the short term, they are prone to calcification and cusp tears, among other failure modes, requiring reoperation and replacement.

Attempts have been made to use synthetic materials, such as polyurethane, among others, as a substitute for the biological tissue, to provide a more durable flexible leaflet prosthetic valve, herein referred to as a synthetic leaflet valve (SLV). However, synthetic leaflet valves have not become a valid valve replacement option since they suffer premature failure, due to, among other things, suboptimal design and lack of a durable synthetic material.

The leaflets move under the influence of fluid pressure. In operation, the leaflets open when the upstream fluid pressure exceeds the downstream fluid pressure and close when the downstream fluid pressure exceeds the upstream fluid pressure. The free edges of the leaflets coapt under the influence of downstream fluid pressure closing the valve to prevent downstream blood from flowing retrograde through the valve.

It has been found that in some very flexible leaflet prosthetic valves, the leaflets do not open and close in a controlled manner. The durability of the leaflets is largely controlled by the character of bending exhibited by the leaflet during the opening-closing cycle. Small radius bends, creases and particularly intersecting creases, can produce high stress zones in the leaflet. These high stress zones can cause the formation of holes and tears under repetitive loading. If the leaflet bending is unrestricted, not only do creases form, but crease intersections lead to formation of large three dimensional structures (e.g., surface disruptions) that oppose bending and slow down the leaflet motion, both in opening and closing. This slow down of leaflet motion leads to an increase in closing volume; that is, the volume of blood that travels back through the valve during the closing phase in order to close the valve. It is advantageous to minimize closing volume.

Further, the flexible nature of the very flexible leaflet can create regions of blood pooling behind the leaflet when in the open position potentially causing blood clots to form at the leaflet base and near the attachment of the leaflet to the frame.

What is needed in the art is a flexible leaflet prosthetic valve that provides a more controlled leaflet movement that reduces closing volume and potential for blood pooling behind the leaflet and near any attachment of the leaflet to a support structure.

SUMMARY

Described embodiments are directed to flexible leaflet prosthetic heart valves in which the leaflets move into the open and closed position in a more controlled manner. Each leaflet moves asymmetrically in that a leaflet second side region of the leaflet initially moves toward the open position before a leaflet first side region and the leaflet first side region initially moves toward the closed position before the leaflet second side region. Further, in the fully open position, the leaflet first side region opens less than the leaflet second side region. Such asymmetric opening and final open position, in synchrony with the other leaflets having the same motion and final open position creates spiral flow exiting the open valve that assists in creating an axial vortex flow that increases blood flow on the downstream side of the leaflet and thus reduces stagnation of the blood that might lead to thrombus formation. Further, controlled asymmetric movement of the leaflet reduces closing volume by initiating closure on the leaflet first side region and finishing closures on the leaflet second side region, reducing leaflet buckling resistance to closure by, in part, allowing one region of the leaflet to close before another region. Further, the leaflet open position is controlled such that fluid flow across the leaflet first side region extends further into the valve orifice of the valve relative to the leaflet second side region to further expose the leaflet downstream side to the retrograde blood flow which increases washout of the blood from the leaflet downstream side and exposes the leaflet downstream side to improved reverse blood flow and to assist closing during the closing phase.

Described embodiments are directed to flexible leaflet prosthetic valves in which the leaflets have regions of increased stiffness relative to other regions of the leaflet, so as to provide asymmetric opening and closing of the leaflet. The region of increased stiffness provides that the leaflet moves into the open and closed position in a more controlled manner. Further, the region of increased stiffness positions the open leaflet so as to provide an increased blood flow behind the leaflet and where the leaflet attaches to the leaflet frame.

In accordance with an embodiment, a prosthetic valve comprises a leaflet frame and a plurality of leaflets coupled to the leaflet frame. Each leaflet has a free edge, a leaflet first side, a leaflet second side, and a leaflet base therebetween. The leaflet first side, leaflet second side, and leaflet base are coupled to the leaflet frame. Each leaflet has a leaflet first side region adjacent the leaflet first side, a leaflet second side region adjacent the leaflet second side, and a leaflet central region therebetween and adjacent the leaflet base. At least a portion of the leaflet first side region has a stiffness that is greater than the stiffness of the leaflet second side region and leaflet central region.

In accordance with another embodiment, a prosthetic valve comprises a frame having a generally tubular shape with attached film. The frame defines a plurality of leaflet windows. Each leaflet window defines a leaflet window first side, a leaflet window second side, and a leaflet window base. The leaflet window first side and the leaflet window second side diverge from the leaflet window base. The film defines at least one leaflet extending from each of the leaflet windows. Each leaflet has a free edge, a leaflet first side that is coupled to the leaflet window first side, a leaflet second side that is coupled to the leaflet window second side, and a leaflet base therebetween that is coupled to the leaflet window base. Each leaflet has a leaflet first side region adjacent the leaflet first side and extending to a substantially axial line from the leaflet free edge to the intersection between the leaflet window first side and the leaflet window base, a leaflet second region adjacent the leaflet second side and extending to a substantially axial line from the leaflet free edge to the intersection between the leaflet window second side and the leaflet window base, and a leaflet central region therebetween and adjacent the leaflet free edge to the leaflet base. At least a portion of the leaflet first side region has a stiffness that is greater than the stiffness of the leaflet second region and leaflet central region.

In accordance with another embodiment, a prosthetic valve comprises a plurality of leaflets where each leaflet includes a leaflet first side region and a leaflet second side region opposite from the leaflet first side region. The leaflet first side region has a thickness that is thicker than a thickness of the second side region.

In accordance with another embodiment, a prosthetic valve comprises a plurality of leaflets where each leaflet includes a leaflet first side and a leaflet second side opposite from the leaflet first side. Each leaflet first side is coupled with the leaflet second side of an adjacent leaflet at a commissure. The plurality of leaflets defines an orifice when the leaflets are in an open position. Each of the leaflet first sides extends further into the orifice than each of the leaflet second sides when the leaflets are in the open position.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 4A is a representation of an embodiment of a leaflet frame of the embodiment of FIG. 3A unrolled to a flat orientation with a strain relief frame covering and leaflet reinforcing member;

FIG. 4B is a representation of an embodiment of a leaflet frame unrolled to a flat orientation of FIG. 3A with a strain relief frame covering and leaflet reinforcing member, also with a leaflet;

DETAILED DESCRIPTION

Figure 1A:
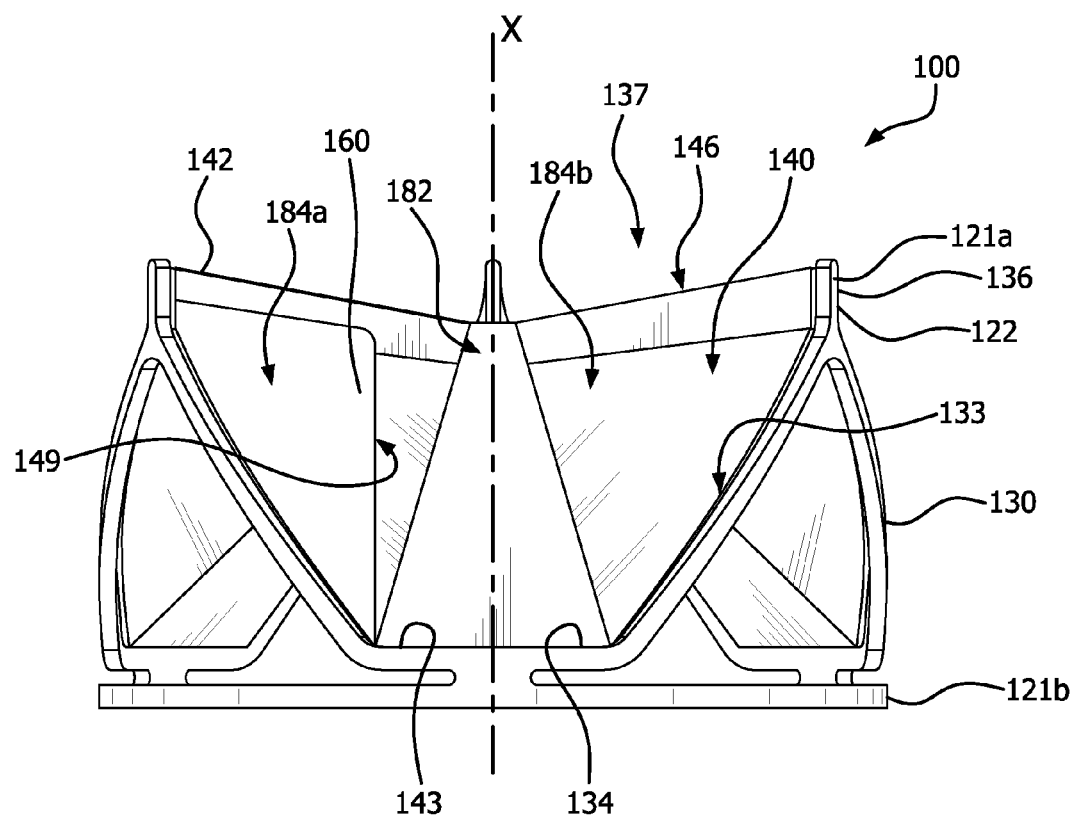
FIG. 1A is a side view of a prosthetic valve in accordance with an embodiment.

Persons skilled in the art will readily appreciate that various aspects of the present disclosure can be realized by any number of methods and apparatus configured to perform the intended functions. Stated differently, other methods and apparatuses can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

The term leaflet as used herein in the context of prosthetic valves is a component of a one-way valve wherein the leaflet is operable to move between an open and closed position under the influence of a pressure differential. In an open position, the leaflet allows blood to flow through the valve. In a closed position, the leaflet substantially blocks retrograde flow through the valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the valve rises above the pressure on the outflow side of the valve, the leaflets opens and blood flows therethrough. As blood flows through the valve into a neighboring chamber or blood vessel, the pressure on the inflow side equalizes with the pressure on the outflow side. As the pressure on the outflow side of the valve rises above the blood pressure on the inflow side of the valve, the leaflet returns to the closed position generally preventing retrograde flow of blood through the valve.

The term membrane as used herein refers to a sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer may be imbibed within a porous structure of the membrane, coated on one or both sides of the membrane, or a combination of coated on and imbibed within the membrane.

The term laminate as used herein refers to multiple layers of membrane, composite material, or other materials, such as elastomer, and combinations thereof.

The term film as used herein generically refers to one or more of the membrane, composite material, or laminate.

The term biocompatible material as used herein generically refers to a film or a biological material, such as, but not limited to, bovine pericardium.

The term leaflet window is defined as that space that a frame defines from which a leaflet extends. The leaflet may extend from frame elements or adjacent to frame elements and spaced apart therefrom.

The terms native valve orifice and tissue orifice refer to an anatomical structure into which a prosthetic valve may be placed. Such anatomical structure includes, but is not limited to, a location wherein a cardiac valve may or may not have been surgically removed. It is understood that other anatomical structures that may receive a prosthetic valve include, but are not limited to, veins, arteries, ducts and shunts. Although reference is made herein to replacing a native valve with a prosthetic valve, it is understood and appreciated that a valve orifice or implant site may also refer to a location in a synthetic or biological conduit that may receive a valve for a particular purpose, and therefore the scope of the embodiments provided herein is not limited to valve replacement.

As used herein, "couple" means to join, connect, attach, adhere, affix, or bond, whether directly or indirectly, and whether permanently or temporarily.

Embodiments herein include various apparatus, systems, and methods for a prosthetic valve suitable for surgical and transcatheter placement, such as, but not limited to, cardiac valve replacement. The valve is operable as a one-way valve wherein the valve defines a valve orifice into which leaflets open to permit flow and close so as to occlude the valve orifice and prevent flow in response to differential fluid pressure.

Described embodiments are directed to flexible leaflet prosthetic valves in which the leaflets move into the open and closed position in a more controlled manner. The leaflets move in synchrony with each other. Each leaflet moves asymmetrically in that a leaflet second side region of the leaflet initially moves toward the open position before a leaflet first side region and the leaflet first side region initially moves toward the closed position before the leaflet second side region. Further, in the fully open position, the leaflet first side opens less than the leaflet second side. The leaflet first side region of one leaflet is adjacent to the leaflet second side region of an adjacent leaflet. Such asymmetric opening and final open position, in synchrony with the other leaflets having the same motion and final open position, creates spiral flow exiting the open valve that assists in creating an axial vortex flow that increases blood flow on the downstream side of the leaflet and thus reduces stagnation of the blood that might lead to thrombus formation. Further, controlled asymmetric movement of the leaflet reduces closing volume by initiating closure on the leaflet first side region and finishing closures on the leaflet second side region, reducing leaflet buckling resistance to closure by, in part, allowing one side region of the leaflet to close before another side region. Further, the leaflet open position is controlled such that the leaflet first side region extends further into the valve orifice of the valve relative to the leaflet second side region to further expose the leaflet downstream side to the retrograde blood flow which increases washout of the blood from the leaflet downstream side and exposes the leaflet downstream side to improved reverse blood flow and to assist closing during the closing phase.

In accordance with embodiments provided herein, at least a portion of the leaflet first side region is configured to be more resistant to motion as compared with the leaflet second side region. The resistant to motion may be affected in a number of ways, including, but not limited to, configuring the bending modulus of the leaflet material to have a higher bending modulus in the leaflet first side region as compared with the leaflet second side region. The resistant to motion may be affected in a number of ways, including, but not limited to, adding a reinforcing member that is separate from but coupled to the leaflet first side region. The resistant to motion may be affected in a number of ways, including, but not limited to, increasing the number of layers of a laminated composite that makes up the leaflet, and thus the thickness in the leaflet first side region as compared with the leaflet second side region.

Embodiments provided herein address controlled leaflet opening and closing. Embodiments provided herein provide a feature of differing leaflet stiffness from one side region of the leaflet to the other side region. The less stiff side region of the leaflet will initiate opening before the stiffer side of the leaflet. Therefore, the leaflet will open asymmetrically with respect to the leaflet free edge rather than symmetrically as with a leaflet having a uniform or symmetric stiffness property. This asymmetric movement minimizes crease formation, which is of particular importance in thin, high-modulus leaflets. If the leaflet bending is unrestricted, not only may creases form, but crease intersections lead to formation of large three dimensional structures (e.g., surface disruptions) that oppose bending and slow down the leaflet motion, both in opening and closing. Embodiments provided herein control leaflet opening and to minimize crease formation provided by the controlled asymmetric opening and closing of the leaflet.

Embodiments provided herein address blood pooling or stagnation that can lead to clot formation behind the leaflet and along the intersection of the leaflet and the frame when the leaflet is open. Embodiments provided herein provide a feature of differing leaflet stiffness from one side region of the leaflet to the other side region. The stiffer side region of the leaflet will open to a lesser extent than the less stiff side region. Since the stiffer side region of the leaflet does not open fully and therefore protrudes into the flow more so than the less stiff side region, retrograde blood flow may better extend behind the leaflet, the downstream side, producing a washing effect along the attachment of the leaflet to the frame and, in particular, at the base of the leaflet on the downstream side of the leaflet. Since the stiffer side region of the leaflet protrudes into the retrograde flow more so than the less stiff side region, when the flow reverses, the stiffer leaflet side region protruding into the flow will actuate the closing of the valve much sooner and in a more controlled manner. Therefore, the leaflet will close asymmetrically from the more stiff side region to the less stiff side region with respect to the leaflet free edge rather than randomly and chaotically as with a very thin and flexible leaflet having a uniform or symmetric stiffness property. This asymmetric movement minimizes crease formation and provides a faster closing response, which is of particular importance in thin, high-modulus leaflets. Embodiments provided herein control leaflet closing that provides minimization of crease formation and a faster closing response provided by the controlled asymmetric closing of the leaflet.

Valve

Figure 1B:
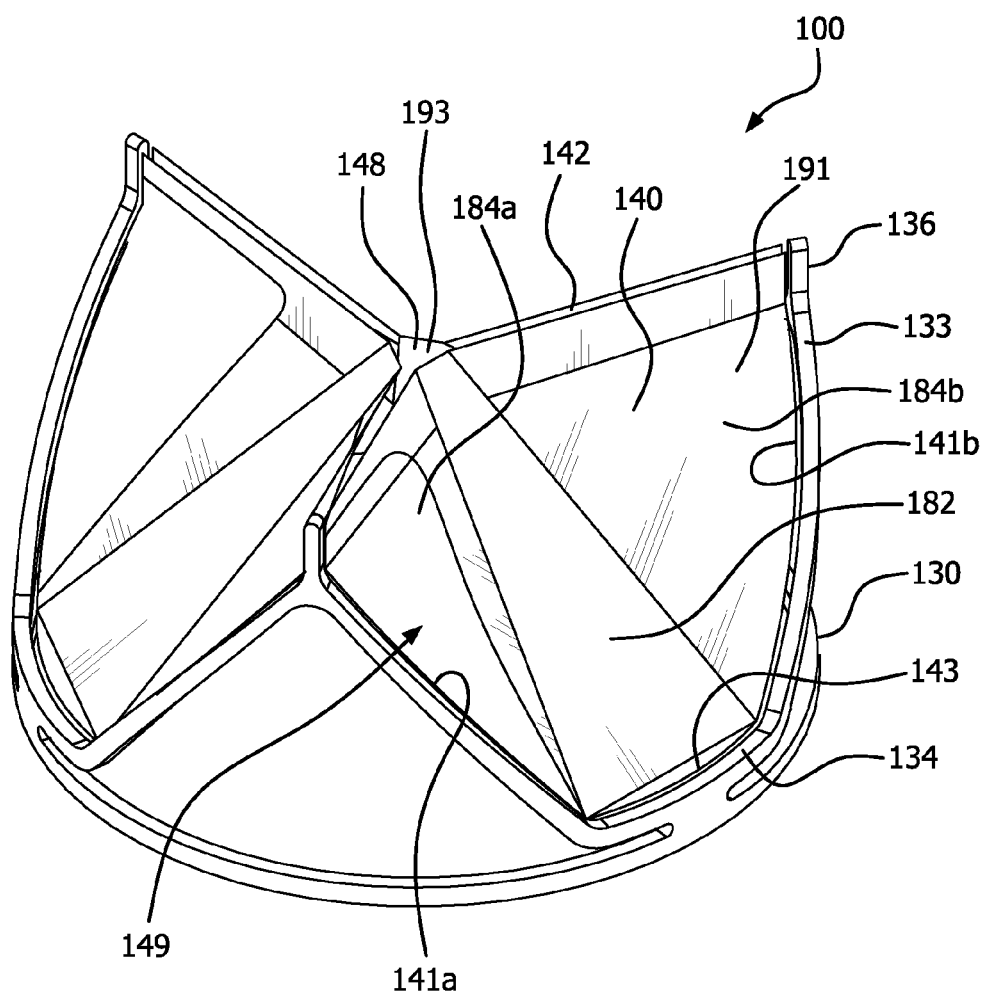
FIG. 1B is a perspective view of the embodiment of the valve of FIG. 1A.
Figure 1C:
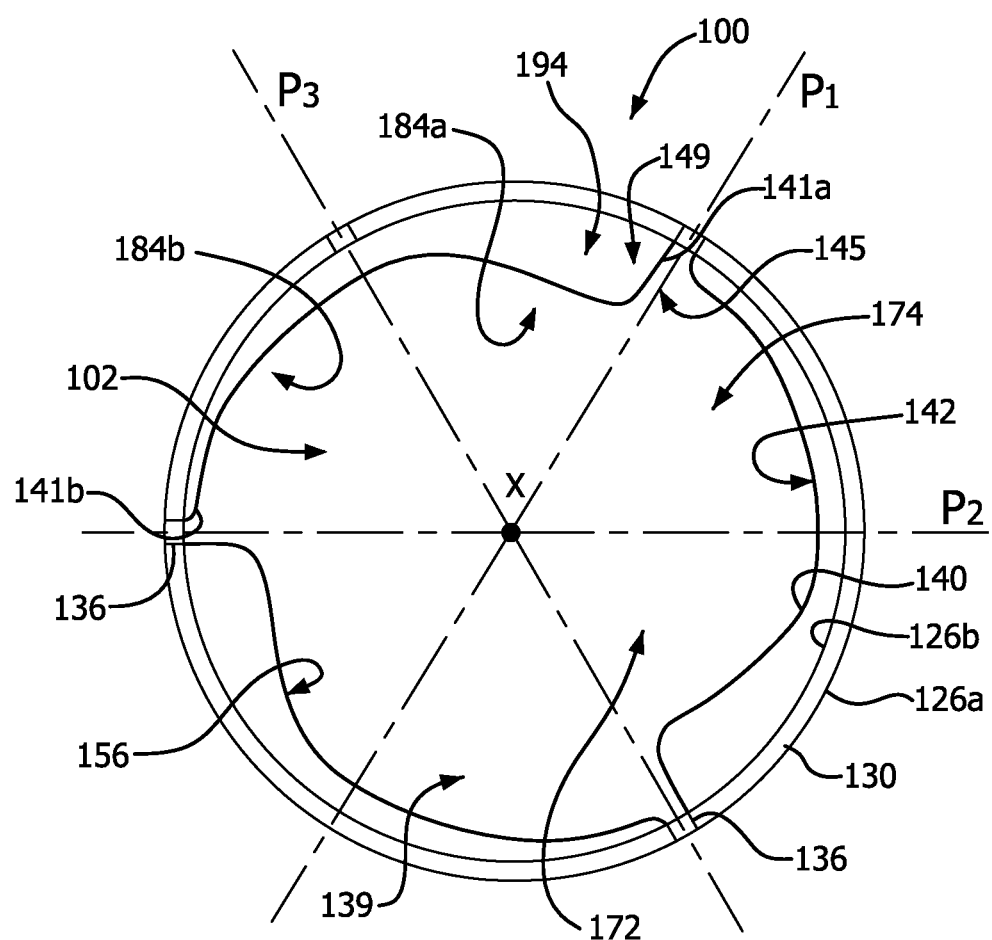
FIG. 1C is an axial view of the embodiment of the valve of FIG. 1A in an open configuration.
Figure 1D:
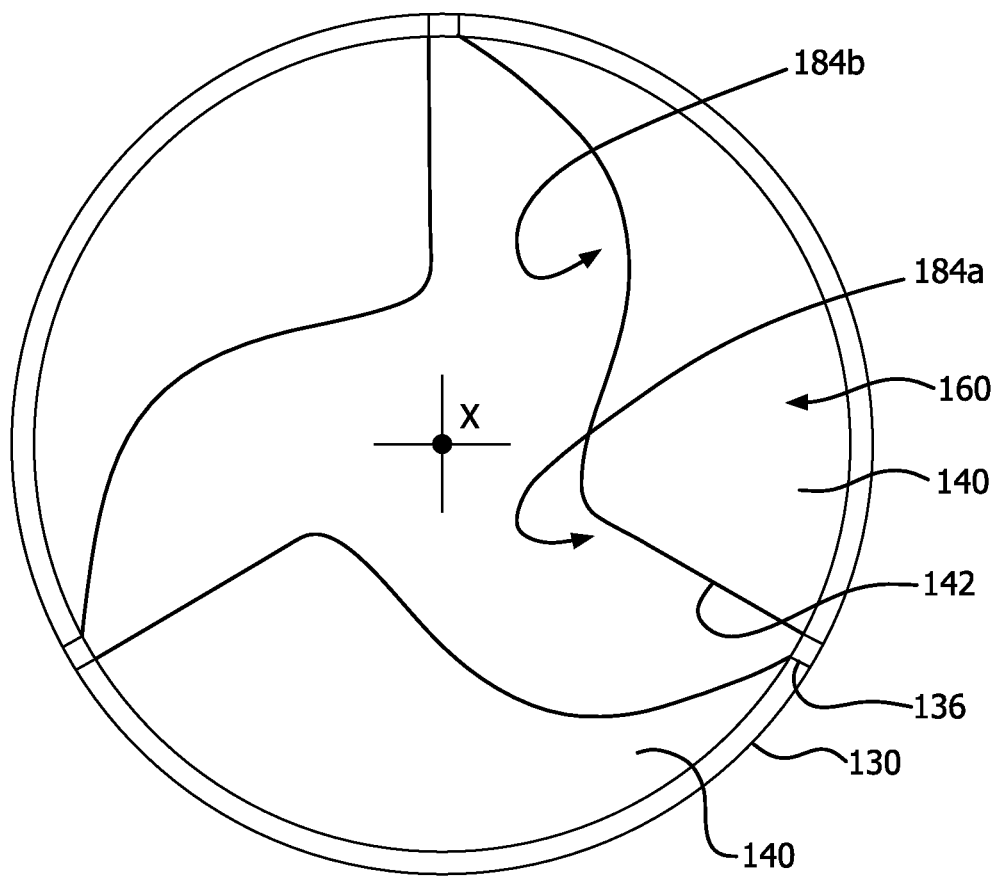
FIG. 1D is an axial view of the embodiment of the prosthetic valve of FIG. 2A in a partially open or partially closed configuration.
Figure 1E:
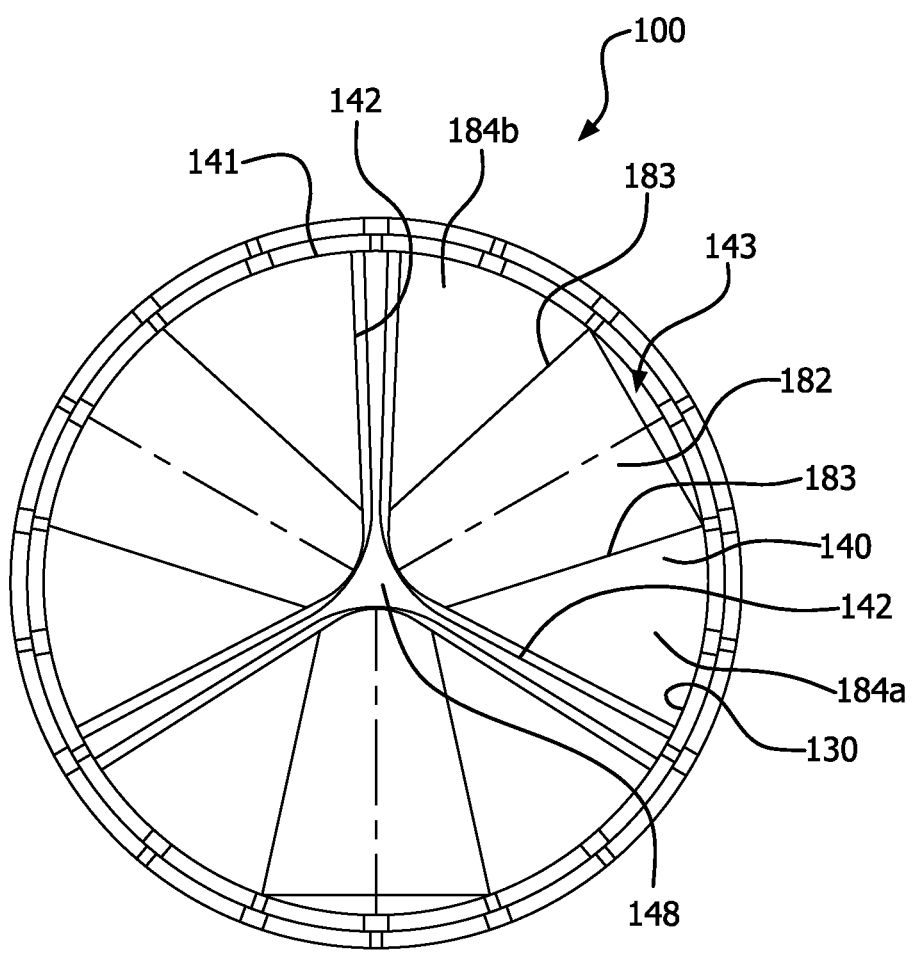
FIG. 1E is an axial view of the embodiment of the prosthetic valve of FIG. 2A in a closed configuration.

FIG. 1A is a side view of a valve 100, in accordance with an embodiment. FIG. 1B is a perspective view of the valve 100 of FIG. 1A. FIGS. 1C, 1D and 1E are axial views of the valve 100 of FIG. 1A in an open, partially open, and closed configuration, respectively. The valve 100 comprises a leaflet frame 130 and film 160 that defines leaflets 140. In FIGS.

1A, 1B and 1E, the leaflets 140 are shown slightly open to better show the features but it is understood that a valve 100 that is fully closed will have the leaflet free edges 142 of the leaflets 140 coming together to coapt under the influence of downstream fluid pressure which results in closing the valve 100 to prevent downstream blood from flowing retrograde through the valve 100.

Frame

Referring to FIGS. 1A-1E, the leaflet frame 130 is a generally tubular member, in accordance with an embodiment. The leaflet frame 130 comprises a leaflet frame first end 121a and a frame second end 121b opposite the leaflet frame first end 121a. The leaflet frame 130 comprises a leaflet frame outer surface 126a and a leaflet frame inner surface 126b opposite the leaflet frame outer surface 126a, as shown in FIG. 1A. The leaflet frame 130 defines commissure posts 136 that couple to the leaflet free edges 142. The commissure posts 136 are defined by a vertical element 122.

Figure 2B:
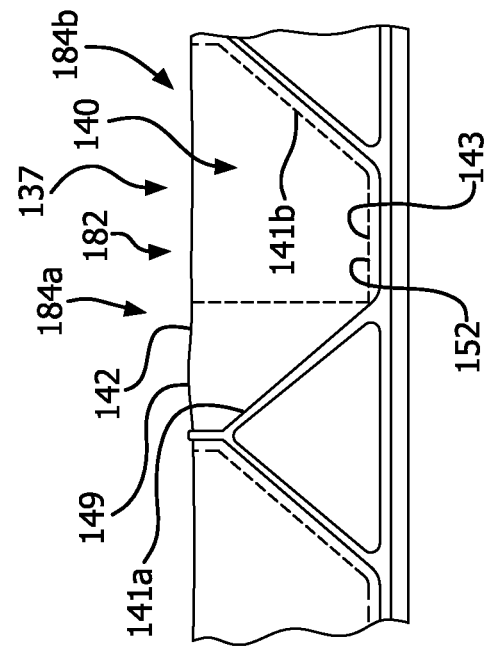
FIG. 2B is a representation of an embodiment of a leaflet frame unrolled to a flat orientation of FIG. 2A with a strain relief frame covering and leaflet reinforcing member, also with a leaflet.
Figure 2A:
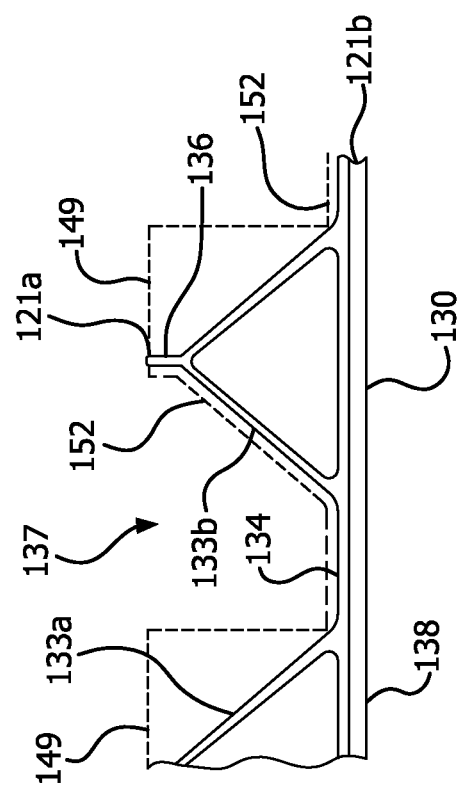
FIG. 2A is a representation of an embodiment of a leaflet frame unrolled to a flat orientation with a strain relief frame covering and leaflet reinforcing member.

FIGS. 2A and 2B are side views of a leaflet frame 130 of a valve 100 wherein the leaflet frame 130 has been longitudinally cut and laid open to better illustrate the elements of the generally tubular-shaped leaflet frame 130, in accordance with an embodiment. In FIG. 2A, a leaflet reinforcing member 149 is shown in dashed line to represent where the leaflet reinforcing member 149 is located within the leaflet window 137, the leaflet window 137 being defined by the leaflet window first side 133a and the leaflet window second side 133b, and the leaflet window base 134. The leaflet reinforcing member 149 is coupled to the leaflet window first side 133a and extends into what will be the leaflet first side region 184a, as shown in FIG. 2B. Also in FIG. 2A, an optional strain relief frame covering 152 is shown in dashed line following the contour of the leaflet window 137. The strain relief frame covering 152 is a covering of film 160 that covers the leaflet frame 130 and extends about 0.5 mm to 1.0 mm into the leaflet window 137. The strain relief frame covering 152 provides a transition region that provides strain relief between the leaflet frame 130 and the leaflet 140.

In FIG. 2B, a leaflet 140 is shown in solid line to represent where the leaflet 140 is located within the leaflet window 137 and the leaflet reinforcing member 149, shown in dashed line, being within the leaflet first side region 184a.

The leaflet frame 130 may comprise a cut tube, or any other element suitable for the particular purpose. The leaflet frame 130 may be etched, cut, laser cut, or stamped into a tube or a sheet of material, with the sheet then formed into a substantially cylindrical structure.

The leaflet frame 130 can comprise any metallic or polymeric material that is biocompatible. For example, the leaflet frame 130 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

Referring to FIGS. 2A and 2B, the leaflet frame comprises a plurality of spaced apart leaflet frame elements defining substantially an isosceles trapezoid interconnected by a base element 138 defining leaflet windows 137. Each of the leaflet window first side 133a and leaflet window second side 133b is defined by a side of one trapezoid and a side of an adjacent trapezoid defining a trapezoidal shape, and wherein each leaflet window base 134 is defined by the base element 138 between the leaflet window first side 133a and leaflet window second side 133b. In the embodiment of FIG. 1B there are three interconnected leaflet windows 137, where a leaflet window first side 133a of one leaflet window 137 is interconnected with an adjacent leaflet window second side 133b of an adjacent leaflet window 137.

Referring again to FIGS. 1A, 2A and 2B, the leaflet frame first end 121a further comprises commissure posts 136 extending from an apex of the leaflet frame elements defining substantially an isosceles trapezoid. The commissure post 136 may affect the leaflet free edge 142 so as to create a larger or wider coaptation region 146 between adjacent leaflet free edges 142.

In accordance with an embodiment, the leaflet frame 130 comprises a frame having a shape determined, at least in part, by wrapping a two dimensional isosceles trapezoid every 120 degrees onto the tubular shape of the leaflet frame 130, the isosceles trapezoid having a leaflet window base 134, a leaflet window first side 133a, and a leaflet window second side 133b that diverge from the leaflet window base 134, and wherein a leaflet window first side 133a and leaflet window second side 133b from adjacent isosceles trapezoids meet at the leaflet frame first end 121a and frame second end 121b, as shown in FIG. 2A. A leaflet 140 is shown located within the leaflet window 137, the leaflet window 137 being defined by the leaflet window first side 133a, the leaflet window second side 133b, and the leaflet window base 134.

In accordance with an embodiment of a valve 100, each leaflet 140 has substantially the shape of an isosceles trapezoid having a leaflet first side 141a and a leaflet second side 141b, a leaflet base 143 and a leaflet free edge 142 opposite the leaflet base 143, wherein the leaflet first side 141a and a leaflet second side 141b diverge from the leaflet base 143, wherein the leaflet base 143 is substantially flat, as shown in dashed lines in FIG. 2B.

Figure 3A:
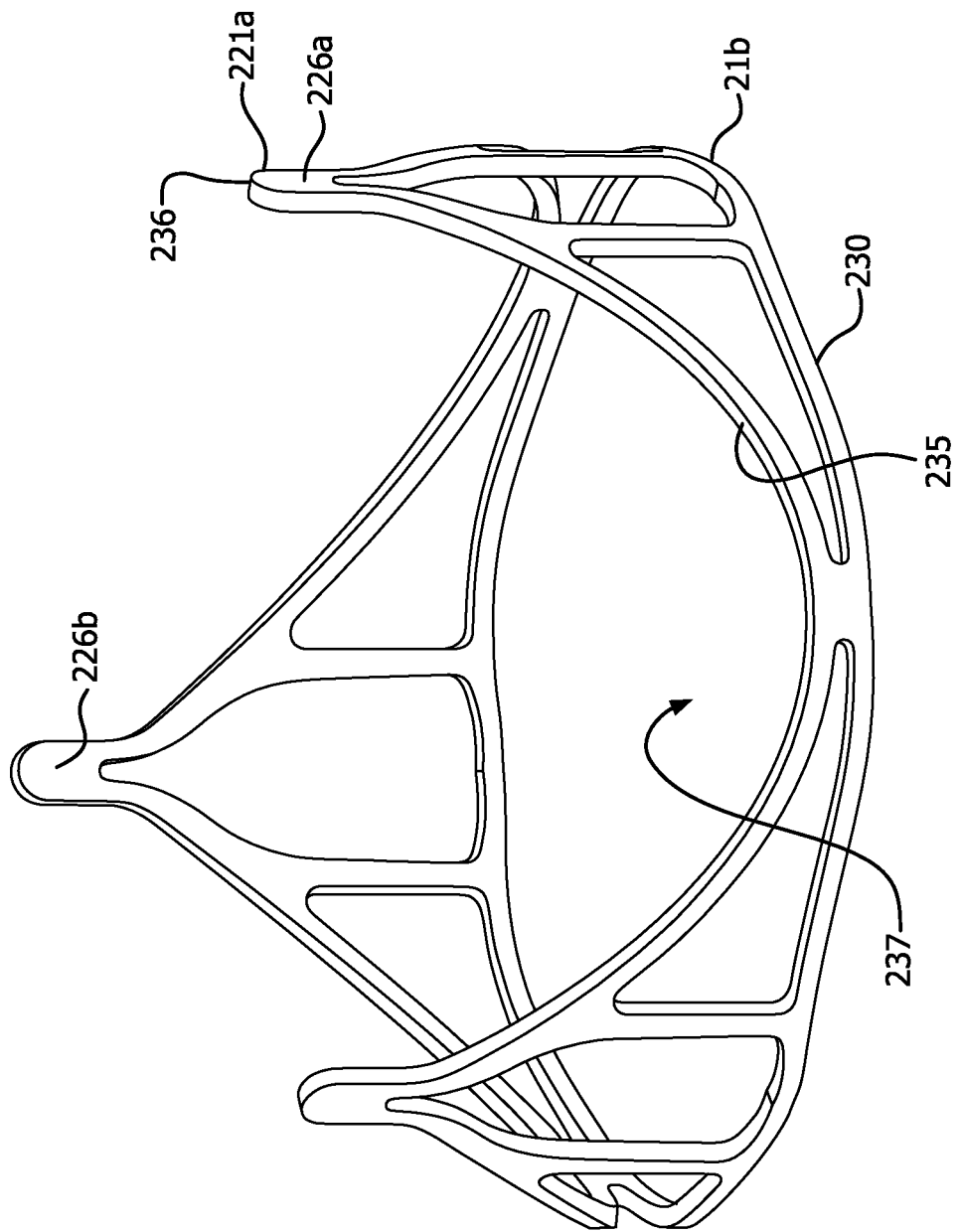
FIG. 3A is a perspective view of another embodiment of a valve frame.

FIG. 3 is a perspective view of a leaflet frame 230 that is a generally tubular member, in accordance with another embodiment. The leaflet frame 230 comprises a frame first end 221a and a frame second end 221b opposite the frame first end 221a. The leaflet frame 230 comprises a leaflet frame outer surface 226a and a leaflet frame inner surface 226b opposite the leaflet frame outer surface 226a, as shown in FIG. 3A. The leaflet frame 230 defines commissure posts 236 that couple to the leaflet free edges 242.

FIGS. 4A and 4B are side views of a leaflet frame 230 of a valve 200 wherein the leaflet frame 230 has been longitudinally cut and laid open to better illustrate the elements of the generally tubular-shaped leaflet frame 230, in accordance with an embodiment. The leaflet frame comprises a plurality of interconnected parabolic leaflet frame elements 235 terminating at commissure posts 236 defining leaflet windows 237. Each parabolic leaflet frame elements 235 may be defined by a leaflet window first side 233a and leaflet window second side 233b on either side of a plane P symmetrically bisecting the parabolic leaflet frame elements 235 aligned with the axial axis X, shown in FIG. 3B.

The commissure posts 236 extend from an apex of intersecting parabolic leaflet frame elements 235. The length of the commissure post 236 may define the length of the coaptation region 146 between adjacent leaflet free edges 142. Where the commissure post 236 is made longer and the leaflet is attached thereto, a larger or wider coaptation region 146 may be defined between adjacent leaflet free edges 142.

In accordance with an embodiment of a valve 200, each leaflet 240 has substantially the shape of a parabola having a leaflet first side 241a including a leaflet first side region 284a and a leaflet second side 241b including a leaflet second side region 284b defined by a plane P symmetrically aligned with the axial axis X bisecting the parabola, and a leaflet free edge 142 between the leaflet first side 241*a* and a leaflet second side 241*b*.

In FIG. 4B, a leaflet reinforcing member 249 is shown in dashed line to represent where the leaflet reinforcing member 249 is located within the leaflet window 237. The leaflet reinforcing member 249 is coupled to the leaflet window first side 233*a* and extends into what will be at least a portion of the leaflet first side region 284*a*. Also in FIG. 4B, an optional strain relief frame covering 252 is shown in dashed line following the contour of the leaflet window 237. The strain relief frame covering 252 is a covering of film 160 that covers the leaflet frame 130 and extends about 0.5 mm to 1.0 mm into the leaflet window 237. The strain relief frame covering 252 provides a transition region that provides strain relief between the leaflet frame 130 and the leaflet 240. In FIG. 14B, a leaflet 240 is shown located within the leaflet window 237 and the leaflet reinforcing member 249 being within the leaflet first side region 284*a*.

Film

The film 160, as shown in FIG. 1A, is generally any sheet-like material that is biologically compatible and configured to couple to the leaflet frame 130, in accordance with embodiments. It is understood that the term "film" is used generically for one or more biocompatible materials suitable for a particular purpose. The leaflets 140 are also comprised of the film 160.

In accordance with an embodiment, the biocompatible material is a film 160 that is not of a biological source and that is sufficiently flexible and strong for the particular purpose, such as a biocompatible polymer. In an embodiment, the film 160 comprises a biocompatible polymer that is combined with an elastomer, referred to as a composite.

Details of various types of film 160 are discussed below. In an embodiment, the film 160 may be formed from a generally tubular material to at least partially cover the leaflet frame 130. The film 160 can comprise one or more of a membrane, composite material, or laminate. Details of various types of film 160 are discussed below.

In an embodiment, the film 160 comprises a biocompatible polymer that is combined with an elastomer, referred to as a composite material. A material according to one embodiment includes a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a laminate while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure for achieving the desired leaflet performance. In accordance with an embodiment, the expanded fluoropolymer comprises a microstructure of nodes interconnected by fibrils, such as described in U.S. Pat. No. 3,953,566 to Gore. The fibrils radially extend from the nodes in a plurality of directions, and the membrane has a generally homogeneous structure. Membranes having this microstructure may typically exhibit a ratio of matrix tensile strength in two orthogonal directions of less than or equal to 2, and possibly less than 1.5.

In another embodiment, the expanded fluoropolymer membrane has a microstructure of substantially only fibrils, as is generally taught by U.S. Pat. No. 7,306,729, to Bacino. The expanded fluoropolymer membrane having substantially only fibrils, can possess a high surface area, such as greater than 20 $m^2/g$, or greater than 25 $m^2/g$, and in some embodiments can provide a highly balanced strength material having a product of matrix tensile strengths in two orthogonal directions of at least $1.5 \times 10^5$ $MPa^2$, and/or a ratio of matrix tensile strengths in two orthogonal directions of less than 4, and possibly less than 1.5.

The expanded fluoropolymer membrane can be tailored to have any suitable thickness and mass to achieve the desired leaflet performance. By way of example, but not limited thereto, the leaflet 140 comprises an expanded fluoropolymer membrane having a thickness of about 0.1 μm. The expanded fluoropolymer membrane can possess a mass per area of about 1.15 $g/m^2$. Membranes according to an embodiment of the invention can have matrix tensile strengths of about 411 MPa in the longitudinal direction and 315 MPa in the transverse direction.

Additional materials may be incorporated into the pores or within the material of the membranes or in between layers of membranes to enhance desired properties of the leaflet. Composite materials described herein can be tailored to have any suitable thickness and mass to achieve the desired leaflet performance. Composite materials according to embodiments can include fluoropolymer membranes and have a thickness of about 1.9 μm and a mass per area of about 4.1 $g/m^2$. In other embodiments, the fluoropolymer membranes have a thickness of about 100 μm and a mass per area of about 100 $g/m^2$.

The expanded fluoropolymer membrane combined with elastomer to form a composite material provides the elements of the present disclosure with the performance attributes required for use in high-cycle flexural implant applications, such as heart valve leaflets, in various ways. For example, the addition of the elastomer can improve the fatigue performance of the leaflet by eliminating or reducing the stiffening observed with ePTFE-only materials. In addition, it may reduce the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment the elastomer is present in a portion of the pores of the at least one fluoropolymer layer. Having elastomer filling the pore volume or present in a portion of the pores reduces the space in which foreign materials can be undesirably incorporated into the composite material. An example of such foreign material is calcium that may be drawn into the membrane from contact with the blood. If calcium becomes incorporated into the composite material, as used in a heart valve leaflet, for example, mechanical damage can occur during cycling open and closed, thus leading to the formation of holes in the leaflet and degradation in hemodynamics.

In an embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675 to Chang et al. As discussed above, the elastomer is combined with the expanded fluoropolymer membrane such that the elastomer occupies substantially all of the void space or pores within the expanded fluoropolymer membrane to form a composite material. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In one embodiment, the composite material comprises three layers: two outer layers of ePTFE and an inner layer of a fluoroelastomer disposed therebetween. Additional fluoroelastomers can be suitable and are described in U.S. Publication No. 2004/0024448 to Chang et al.

In another embodiment, a method of filling the pores of the expanded fluoropolymer membrane includes the steps of delivering the filler via a dispersion to partially or fully fill the pores of the expanded fluoropolymer membrane.

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675 to Chang et al., and other references that would be known to those of skill in the art. Other biocompatible polymers which can be suitable for use in leaflet 140 include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Leaflet

Each leaflet window 137 is provided with a biocompatible material, such as a film 160, which is coupled to a portion of the leaflet window sides 133 with the film 160 defining a leaflet 140, as shown in FIGS. 1A-1D and 2B. Each leaflet 140 defines a leaflet free edge 142 and a leaflet base 143, in accordance with an embodiment. As will be described below, it is anticipated that a plurality of embodiments of leaflet shapes, including with and without a defined leaflet base 143, may be provided. In accordance with an embodiment, the film 160 is coupled to at least a portion of the leaflet window first side 133a and leaflet window second side 133b and to the leaflet window base 134 where the leaflet 140 is defined by the portion of the leaflet window first side 133a, the leaflet window second side 133b and to the leaflet window base 134. The leaflet 140 has a leaflet upstream side 193 and a leaflet downstream side 191 opposite the leaflet upstream side 193. The leaflet upstream side 193 is that side of the leaflet 140 that is facing away from the leaflet frame 130 when in the open position and the leaflet downstream side 191 is that side of the leaflet 140 that is facing toward the leaflet frame 130 when in the open position.

When the leaflets 140 are in a fully open position, the valve 100 presents a substantially circular valve orifice 102 as shown in FIG. 1C. Fluid flow is permitted through the valve orifice 102 when the leaflets 140 are in the open position. Since the leaflet first side region 184a is stiffer than the leaflet second side region 184b, the leaflet first side region 184a does not open fully leaving a pocket 194 defined in part by the leaflet downstream side 191 adjacent the leaflet first side region 184a. As the blood exits the valve 100, retrograde flow may enter the pocket 194 so as to wash out the area defined by the leaflet downstream side 191.

A geometric orifice area (GOA), as is known in the art, is an area measurement of an axial projection of an open area defined by the valve when in the fully open position. As explained below, a first portion of a leaflet will extend further into the valve orifice defined by the valve frame, that is, not open as much, than a second portion of the same leaflet, which opens further. From an axial viewpoint, the first portion of the leaflet will create a smaller GOA than the second portion of the leaflet FIG. 1C is an axial view of the valve 100 in the fully open position. As shown in FIG. 1C, the leaflets 140 do not completely open to conform to the leaflet frame inner surface 126b, therefore projecting a smaller geometric orifice area compared with an orifice area of a frame without leaflets. The leaflet frame inner surface 126b in cross-section transverse to the X axis defines a frame orifice 139 having a frame orifice area that is circular in shape.

The axial view shown in FIG. 1C is bisected into six segments by three planes P1, P2, P3 where each plane passes through one commissure post 136, the axis X and bisects a leaflet 140 in half, defining a first segment 172 and a second segment 174. The leaflet first side region 184a of the leaflet 140 in the first segment 172 extends more into the frame orifice 139 defined by the leaflet frame inner surface 126b defining a smaller GOA, for example, up to 70 percent smaller, than the leaflet second side region 184b in the second segment 174. The benefit of this relationship of the leaflet first side region 184a extending into the valve orifice as compared to the leaflet second side region 184b will be detailed below.

FIG. 1D is an axial view of the valve 100 in the partially open position or a partially closed position. The leaflet first side region 184a of one leaflet 140 is adjacent to the leaflet second side region 184b of an adjacent leaflet 140. The leaflet first side region 184a is stiffer compared to the leaflet second side region 184b. The leaflet second side region 184b will initially open first and will close last compared to the leaflet first side region 184a. This controlled motion provides a consistent leaflet motion from cycle to cycle imparting the benefits previously described.

As the leaflets 140 cycle between the open and closed positions, the leaflets 140 generally flex about the leaflet base 143 and the portion of the leaflet window first side 133a and the leaflet window second side 133b to which the leaflets 140 are coupled. Since the leaflet first side region 184a is more stiff than the leaflet second side region 184b, the leaflet first side 141a does not flex as much about the leaflet window first side 133a as compared with the leaflet second side 141b defining a channel 145 between the leaflet first side 141a of one leaflet 140 and the leaflet second side 141b of an adjacent leaflet 140 when the leaflet is not in the closed position. The channel 145 is defined when the leaflet 140 moves from the closed position. The channel 145 allows for blood flow therethrough throughout the opening phase of the leaflet 140 and thus reduces the potential for blood pooling, stagnation and clot formation between the leaflet first side 141a and the leaflet window first side 133a, and the leaflet second side 141b and the leaflet window second side 133b, and therebetween.

When the valve 100 is closed, generally about half of each leaflet free edge 142 abuts an adjacent half of a leaflet free edge 142 of an adjacent leaflet 140, as shown in FIG. 1E. The three leaflets 140 of the embodiment of FIG. 1E meet at a triple point 148. The valve orifice 102 is occluded when the leaflets 140 are in the closed position stopping fluid flow. Although the leaflet first side region 184a is stiffer than the leaflet central region 182 and the leaflet second side region 184b, the flexibility of the leaflet central region 182 and the leaflet second side region 184b of an adjacent leaflet 140 allows for coaptation with the leaflet first side region 184a allowing for proper closing of the valve 100.

Referring to FIG. 1E, in accordance with an embodiment, each leaflet 140 includes a leaflet central region 182, a leaflet first side region 184a, and a leaflet second side region 184b on opposite sides of the leaflet central region 182. The leaflet central region 182 is defined by a shape substantially that of a rectangle defined by two leaflet central region sides 183, the leaflet base 143 and the leaflet free edge 142. The two leaflet central region sides 183 extend from the leaflet base 143 to the leaflet free edge 142.

In accordance with an embodiment, the leaflet first side region 184a is stiffer than the leaflet central region 182 and the leaflet second side region 184b. The stiffness characteristics of the leaflet first side region 184a, leaflet second side region 184b and the leaflet central region 182 may be affected by any suitable means. In accordance with an embodiment, the leaflet 140 comprises a film that is a laminate of multiple layers of composite material. Additional layers of composite material are provided in the leaflet first side region 184a which imparts additional stiffness to the leaflet first side region 184a as compared with the leaflet central region 182 and the leaflet second side region 184b. Example 1 provides additional details as to the embodiment just described.

Referring to the embodiment of FIGS. 3A, 3B and 4A, 4B, in contrast to the embodiment of FIGS. 1B, 2A and 2B, the parabolic shaped leaflet window 237 does not define a distinct base but only a leaflet window first side 233a and leaflet window second side 233b on either side of a plane P symmetrically bisecting the parabolic leaflet frame elements 235 aligned with the axial axis X, shown in FIGS. 4A and 4B. Therefore, the film 160 is coupled to at least a portion of the leaflet window first side 233a and leaflet window second side 233b where the leaflet 240 is defined by the portion of the leaflet window first side 233a and the leaflet window second side 133b. The leaflet 240 has a leaflet upstream side 193 and a leaflet downstream side 191 opposite the leaflet upstream side 193. The leaflet upstream side 193 is that side of the leaflet 140 that is facing away from the leaflet frame 230 when in the open position and the leaflet downstream side 191 is that side of the leaflet 240 that is facing toward the leaflet frame 130 when in the open position.

The embodiments of FIGS. 1A-E and 3, 4A and 4B are examples of two different leaflet and leaflet window geometries that are suitable for the particular purpose. It is understood that other leaflet and leaflet window geometries may also be suitable for the particular purpose and are not limited thereto.

Figure 3B:
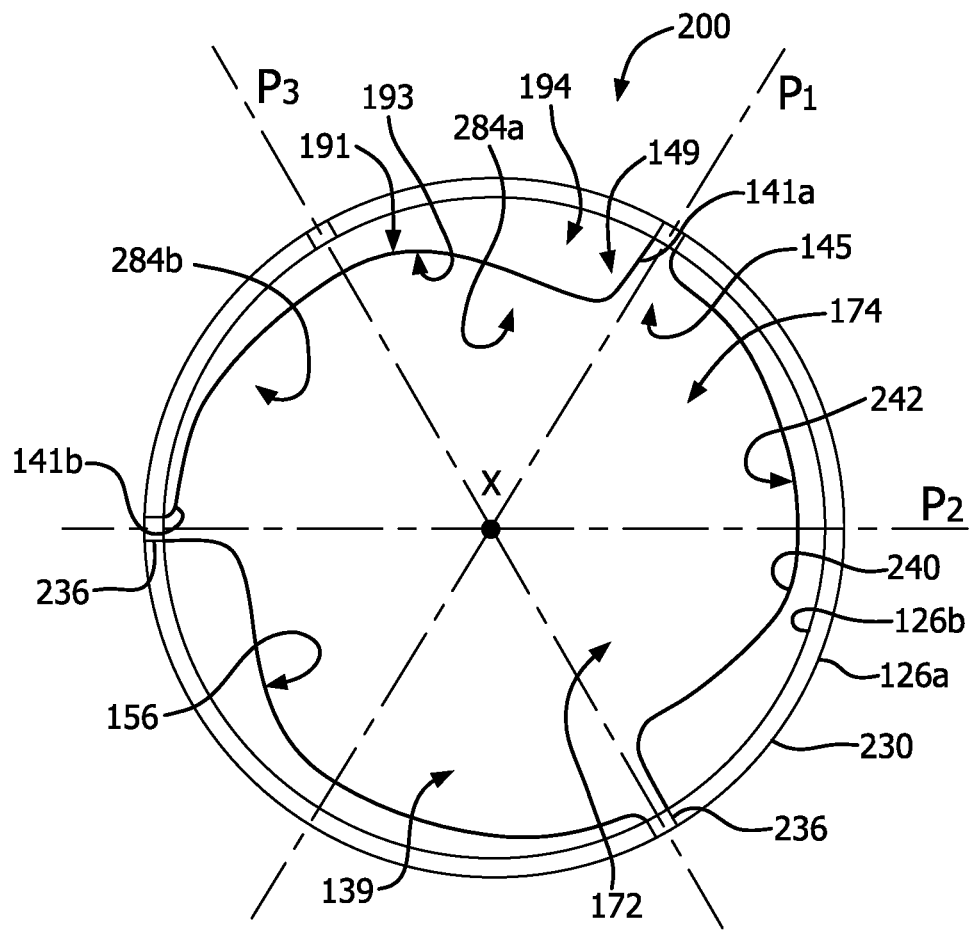
FIG. 3B is an axial view of the embodiment of the valve of FIG. 3A in an open configuration.

The axial view of the valve 200 shown in FIG. 3B is bisected into six segments by three planes P1, P2, P3 where each plane passes through one commissure post 236, the axis X and bisects a leaflet 240 in half, defining a first segment 172 and a second segment 174. The portion of the leaflet in the first segment 172 defines a smaller GOA than the portion of the leaflet in the second segment 174, by virtue of the leaflet first side region 284a extending further into the frame orifice 139 defined by the leaflet frame inner surface 126b.

FIG. 3B is an axial view of the valve 200 in the partially open position or a partially closed position. The leaflet first side region 284a of one leaflet 240 is adjacent to the leaflet second side region 284b of an adjacent leaflet 240. The leaflet first side region 284a is stiffer compared to the leaflet second side region 284b. The leaflet second side region 284b will initially open first and will close last compared to the leaflet first side region 284a. This controlled motion provides a consistent leaflet motion from cycle to cycle imparting the benefits previously described.

The leaflet 140 can be configured to actuate at a pressure differential in the blood caused, for example, by the contraction of a ventricle or atrium of the heart, such pressure differential typically resulting from a fluid pressure building up on one side of the valve 100 when closed. As the pressure on an inflow side of the valve 100 rises above the pressure on the outflow side of the valve 100, the leaflet 140 opens and blood flows therethrough. As blood flows through the valve 100 into a neighboring chamber or blood vessel, the pressure equalizes. As the pressure on the outflow side of the valve 100 rises above the blood pressure on the inflow side of the valve 100, the leaflet 140 returns to the closed position generally preventing the retrograde flow of blood through the inflow side of the valve 100.

It is understood that the leaflet frame 130 may comprise any number of leaflet windows 137, and thus leaflets 140, suitable for a particular purpose, in accordance with embodiments. Leaflet frames 130 comprising one, two, three or more leaflet windows 137 and corresponding leaflets 140 are anticipated.

Although embodiments provided above comprise a leaflet frame that supports the leaflets, it is understood and appreciated that the leaflets may not necessarily be supported by a frame. In accordance with an embodiment, the leaflets may be supported by the inner wall within a solid-walled conduit without a frame that defines leaflet windows and commissure posts. In other embodiments, the leaflets may be constructed as in the tissue valve art that are formed into the desired shape without a frame.

In another embodiment of a valve including a plurality of leaflets, each leaflet includes a leaflet first side and a leaflet second side opposite from the leaflet first side. Each leaflet first side is coupled with the leaflet second side of an adjacent leaflet at a commissure. The plurality of leaflets defines an orifice, also referred to as a lumen, when the leaflets are in an open position. Each of the leaflet first sides extend further into the orifice than each of the leaflet second sides.

In another embodiment, a prosthetic valve comprises a plurality of leaflets. Each leaflet includes a leaflet first side region and a leaflet second side region opposite from the leaflet first side region. Each leaflet defines a leaflet base and a leaflet free edge opposite from the leaflet base. Each leaflet first side region is coupled with the leaflet second side region of an adjacent leaflet at a commissure. The leaflet base of the plurality of leaflets defines an orifice. The leaflet second side regions extend further into the orifice than the leaflet first side region when the leaflets are in the fully open position.

In another embodiment, a prosthetic valve comprises a plurality of leaflets. Each leaflet includes a leaflet first side region and a leaflet second side region opposite from the leaflet first side region. At least a first portion of the leaflet first side region has a first thickness and the leaflet second side region has a second thickness wherein the first thickness is greater than the second thickness. In operation, each leaflet opens asymmetrically. In one embodiment, the first thickness may be ten times greater than the second thickness.

In another embodiment, a prosthetic valve comprises a plurality of leaflets. Each leaflet includes a leaflet first side region and a leaflet second side region opposite from the leaflet first side region. The leaflet first side region has a first bending stiffness and the leaflet second side region has a second bending stiffness. The first bending stiffness is greater than the second bending stiffness. In operation, each leaflet opens asymmetrically.

In another embodiment, a prosthetic valve comprises a plurality of leaflets. Each leaflet includes a leaflet first side region and a leaflet second side region opposite from the leaflet first side region. The leaflet first side region being more resistant to moving compared with the leaflet second side region. In operation, each leaflet opens asymmetrically.

In another embodiment, a prosthetic valve comprises a plurality of leaflets. Each leaflet includes a leaflet first side region and a leaflet second side region opposite from the leaflet first side region. The leaflet first side region being slower to open compared with the leaflet second side region. In operation, each leaflet opens asymmetrically.

In another embodiment, a prosthetic valve comprises a plurality of leaflets. Each leaflet includes a leaflet first side region and a leaflet second side region opposite from the leaflet first side region. Each leaflet defines a leaflet base and a leaflet free edge opposite from the leaflet base. Each leaflet first side region is coupled with the leaflet second side region of an adjacent leaflet at a commissure. The leaflet base of the plurality of leaflets defines an orifice. At least one of the leaflet second side regions extends further into the orifice than the leaflet first side region when the leaflets are in the fully open position.

In another embodiment, a prosthetic valve comprises a plurality of leaflets. At least one leaflet includes a leaflet first side region and a leaflet second side region opposite from the leaflet first side region. The leaflet first side region has a first thickness and the leaflet second side region has a second thickness. The first thickness is greater than the second thickness.

In another embodiment, a prosthetic valve comprises a plurality of leaflets. Each leaflet includes a leaflet first side region and a leaflet second side region opposite from the leaflet first side region. At least one of the leaflets has a leaflet first side region having a first bending stiffness and the leaflet second side region having a second bending stiffness, wherein the first bending stiffness is greater than the second bending stiffness.

In another embodiment, a prosthetic valve comprises a plurality of leaflets. Each leaflet includes a leaflet first side region and a leaflet second side region opposite from the leaflet first side region. At least one of the leaflets presents with the leaflet first side region being more resistant to moving compared with the leaflet second side region.

In another embodiment, a prosthetic valve comprises a plurality of leaflets. Each leaflet includes a leaflet first side region and a leaflet second side region opposite from the leaflet first side region. At least one of the leaflets presenting the leaflet first side region being slower to open compared with the leaflet second side region.

In another embodiment, a prosthetic valve comprises a plurality of leaflets. Each leaflet includes a leaflet first side region and a leaflet second side region opposite from the leaflet first side region. At least one leaflet has a thickness that tapers from the leaflet first side region to the leaflet second side region.

In another embodiment, a prosthetic valve comprises a plurality of leaflets. Each leaflet includes a leaflet first side region and a leaflet second side region opposite from the leaflet first side region. At least one leaflet has a thickness that varies from the leaflet first side region to the leaflet second side region.

One skilled in the art will appreciate that the leaflet embodiments provided herein may be applied to any prosthetic valve design regardless as to how the leaflets are supported to function as described.

Other Considerations

In accordance with an embodiment, the valve 100 can be configured to prevent interference with a heart conduction system by not covering a bundle branch in the left ventricle when implanted, such as might be encountered with an aortic valve replacement procedure. For example, the valve 100 can comprise a length of less than about 25 mm or less than about 18 mm. The valve 100 can also comprise an aspect ratio of less than one, wherein the ratio describes the relationship between the length of the valve 100 to the expanded, functional diameter. However, the valve 100 can be constructed at any length and, more generally, any desirable dimension.

Sewing Cuff

In accordance with a valve 100 suitable for surgical implantation, the valve 100 further comprises a sewing cuff about a leaflet frame 130 in accordance with an embodiment. The sewing cuff is operable to provide structure that receives suture for coupling to the implant site. The sewing cuff may comprise any suitable material, such as, but not limited to, double velour polyester. The sewing cuff may be located circumferentially around a perimeter of the base of the leaflet frame 130. Sewing cuffs are known in the art.

The valve 100 can further comprise a bio-active agent. Bio-active agents can be coated onto a portion or the entirety of the film 160 for controlled release of the agents once the valve 100 is implanted. The bio-active agents can include, but are not limited to, vasodilator, anti-coagulants, anti-platelet, anti-thrombogenic agents such as, but not limited to, heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Method of Making

Embodiments described herein also pertain to a method of making the valve 100 embodiments as described herein. In order to make the various embodiments, a mandrel 710 that is cylindrical can be used. With reference to FIGS. 3A-3C, the mandrel 710 comprises a structural form operable to receive the leaflet frame 130 thereon.

Figure 5A:
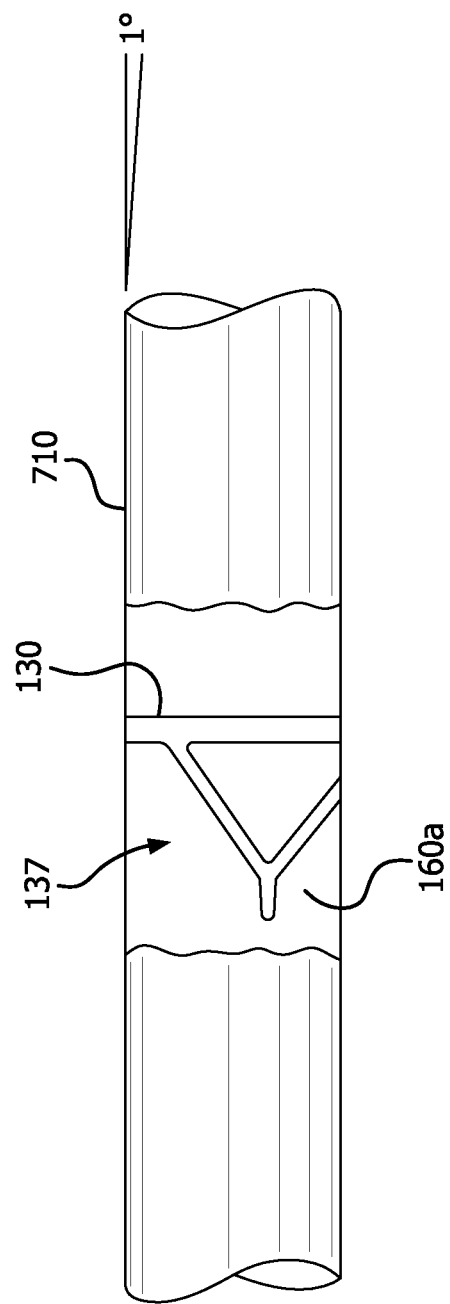
FIG. 5A is a side view of the leaflet frame on an assembly mandrel, in accordance with an embodiment.
Figure 5B:
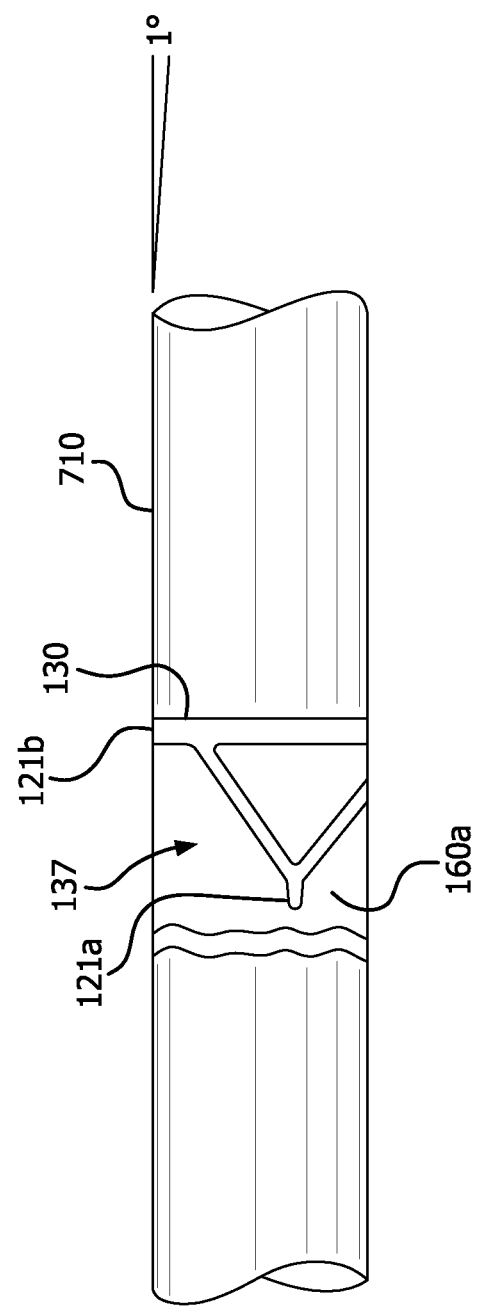
FIG. 5B is a side view of the leaflet frame on an assembly mandrel, in accordance with an embodiment.
Figure 5C:
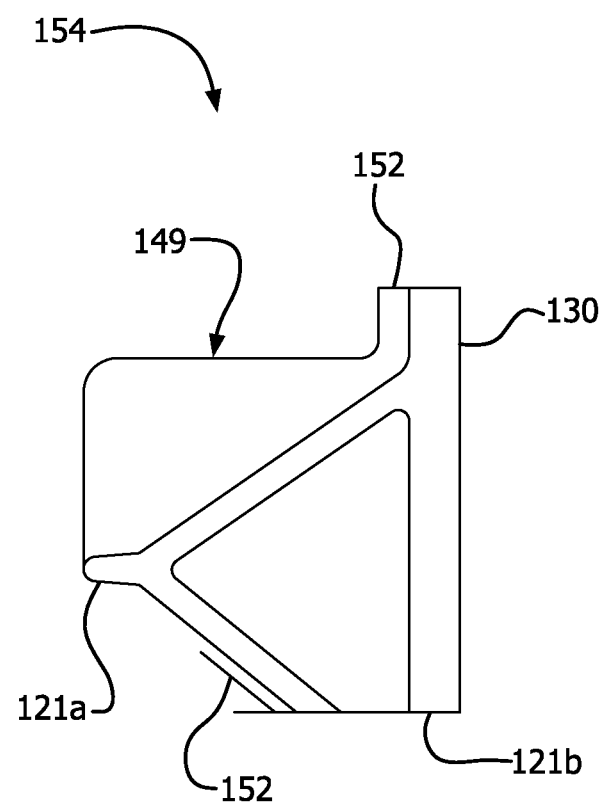
FIG. 5C is a side view of the leaflet frame construct showing the strain relief frame covering and leaflet reinforcing member, in accordance with an embodiment.
Figure 6A:
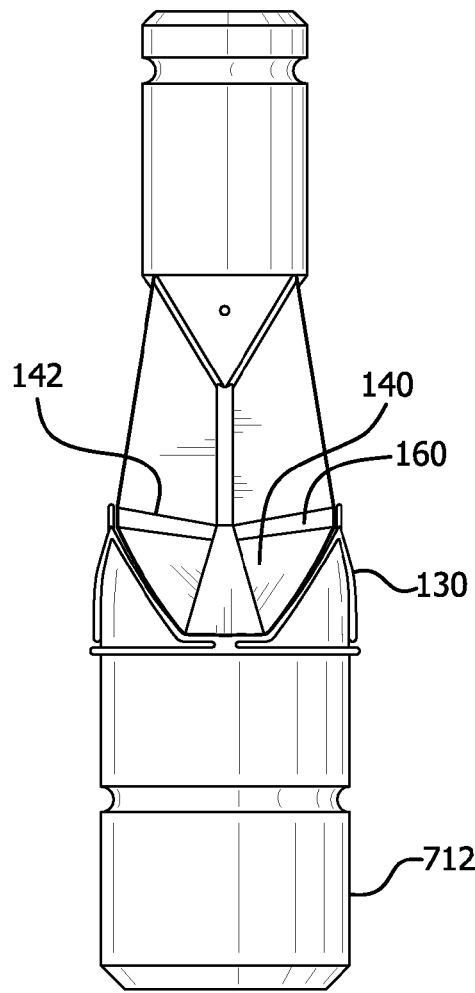
FIG. 6A is a side view of the leaflet frame on a mandrel, in accordance with an embodiment.
Figure 6B:
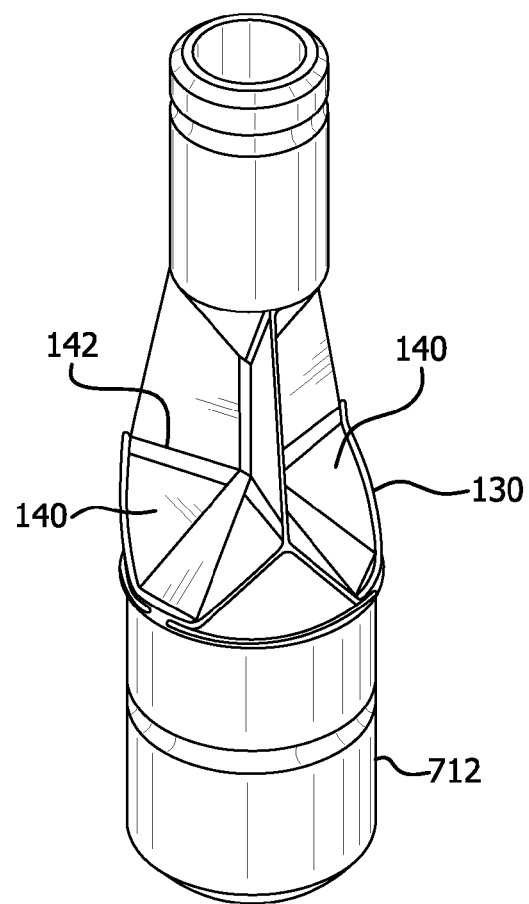
FIG. 6B is a perspective view of the leaflet frame on the mandrel of FIG. 6A.

An embodiment of a method of making a valve 100 comprises the steps of wrapping a first film layer 160a, e.g., a composite as described herein, into a tubular form about the mandrel 710; placing the leaflet frame 130 over the first film layer 160a, as shown in FIG. 5A; thermally setting the assembly; trimming the first film layer 160a to define a leaflet reinforcing member 149 that is at least a portion of the leaflet first side region adjacent to and depending from the leaflet window first side 133a and removing the first film layer 160a from the leaflet window that substantially defines the leaflet central region 182 and the leaflet second side region 184b; trimming the first film layer 160a to within about 0.5 to 1.0 mm of the leaflet window second side 133b and the leaflet window base 134 within the leaflet window 137, as shown in FIG. 5B; define at least a portion of the leaflet first side region and removing the first film layer 160a from the leaflet window that substantially defines the leaflet central region 182 and the leaflet second side region 184b, as shown in FIG. 5B; forming a second film layer 160b over the leaflet frame 130, as shown in FIG. 5C; thermally setting the assembly; receiving the assembly over a mandrel 712 as shown in FIGS. 6A and 6B; cutting the film 160 across the leaflet window top within the leaflet window 137.

The resulting valve 100 comprises a leaflet 140 having a leaflet first side region 184a that includes a leaflet reinforcing member 149 that is the first film layer 160a coupled to the second film layer 160b, and the leaflet central region 182 and leaflet second side region that only includes the second film layer 160b. A small border of the first film layer 160a that depends from the leaflet window second side 133b and the leaflet window base 134 within the leaflet window 137 provides a strain relief that reduces the strain in the leaflet 140 at the interface between the leaflet 140 and the leaflet window 137 of the leaflet frame 130.

Example

In an embodiment, a heart valve having polymeric leaflets formed from a composite material having an expanded fluoropolymer membrane and an elastomeric material and joined to a metallic frame, and further a having a strain relief frame covering and a leaflet reinforcing member was constructed according to the following process:

A leaflet frame 130 was laser machined from a length of MP35N cobalt chromium tube hard tempered with an outside diameter of 23.0 mm and a wall thickness of 0.6 mm. The leaflet frame was electro-polished resulting in 0.01 mm material removal from each surface and leaving the edges rounded. The leaflet frame was cleaned by submersion in an ultrasonic bath of acetone for approximately five minutes.

A strain relief was attached to the leaflet frame in the following manner. A steel metal mandrel having tape red diameter of 21.5 mm to 22.0 mm outer diameter (taper angle of 0.1 degrees) was obtained. A thin-walled (122 µm) sintered 15 mm diameter ePTFE tube was disposed on the metal mandrel by stretching radially over another tapered mandrel and transferring to the 21.5 mm to 22.0 mm mandrel. One layer of a substantially nonporous ePTFE membrane with an FEP coating was circumferentially wrapped on the mandrel with the FEP side towards the mandrel. This membrane was adhered by tacking using a soldering iron (Weller) set to 400° C., thereby creating a covered mandrel. The ePTFE and substantially nonporous ePTFE membrane combined to serve as an inner release liner. This entire release liner was removed in a later step.

A composite material comprising a membrane of ePTFE imbibed with a fluoroelastomer was obtained. The composite material was comprised of three layers: two outer layers of ePTFE and an inner layer of a fluoroelastomer disposed therebetween. The ePTFE membrane was manufactured according to the general teachings described in U.S. Pat. No. 7,306,729. The fluoroelastomer was formulated according to the general teachings described in U.S. Pat. No. 7,462,675.

The ePTFE membrane had the following properties: thickness=about 15 µm; MTS in the highest strength direction=about 400 MPa; MTS strength in the orthogonal direction=about 250 MPa; Density=about 0.34 g/cm$^3$; IBP=about 660 KPa.

The fluoroelastomer consists essentially of between about 65 and 70 weight percent perfluoromethyl vinyl ether and complementally about 35 and 30 weight percent tetrafluoroethylene.

The percent weight of the fluoroelastomer relative to the ePTFE was about 53%.

The multi-layered composite had the following properties: thickness of about 40 µm; density of about 1.2 g/cm$^3$; force to break/width in the highest strength direction=about 0.953 kg/cm; tensile strength in the highest strength direction=about 23.5 MPa (3,400 psi); force to break/width in the orthogonal direction=about 0.87 kg/cm; tensile strength in the orthogonal direction=about 21.4 MPa (3100 psi), IPA bubble point greater than about 12.3 MPa, Gurley Number greater than about 1,800 seconds, and mass/area=about 14 g/m$^2$.

Ten layers of this composite material was circumferentially wrapped on top of the covered mandrel, and tacked with a soldering iron. One layer of film consisting of only the above described fluoroelastomer (0.04 mm) was then wrapped on top of the previously applied film and tacked with a soldering iron, thereby creating a leaflet frame covering. For this tacking operation, a 0.03 mm thick polyimide film (Kapton polyimide, 2271 K1, McMaster-Carr, Santa Fe Springs Calif.) was temporarily placed between the fluoroelastomer film and the iron to prevent the fluoroelastomer film from adhering to the iron.

The clean leaflet frame was then placed over the leaflet frame covering on the mandrel from the small diameter side of the taper until it fit snugly, with the base of the frame toward the small diameter portion of the taper, as shown in FIG. 5A.

The leaflet frame covering that extended beyond the base of the frame toward the small taper was then everted over the frame until the entire frame was encapsulated and the folded edge of the everted material was flush with the base of the frame to create an outer leaflet frame covering, as shown in FIG. 5B.

Approximately ten layers of a sacrificial longitudinally expanded PTFE film having a thickness of about 0.1 mm were tightly wrapped around the covered frame. The resulting assembly was then placed in a convection oven set at 320° C. for 20 minutes. This assembly was removed from the oven and allowed to cool, and the outer sacrificial layers were removed. This assembly was then removed from the mandrel, ensuring that it was released from the inner sacrificial layer.

Using a surgical blade, the leaflet frame cover was trimmed, as shown in FIG. 2B, to create a construct 154 consisting of a leaflet frame 130, a leaflet reinforcing member 149 adjacent to one side of each post and a strain relief frame covering 152. The remainder of the frame covering was trimmed at 1 mm from the edge of the frame, leaving 6 mm leaflet reinforcing member 149 on one side of each post, as shown in FIG. 5C, the leaflet window first side 133a, as shown in FIG. 2A.

A leaflet material was then prepared having a membrane layer of ePTFE imbibed with a fluoroelastomer. More specifically, the membrane layer of ePTFE was manufactured according to the general teachings described in U.S. Pat. No. 7,306,729. The ePTFE membrane was tested in accordance with the methods described below. The ePTFE membrane had a mass per area of about 0.6 g/m$^2$, a porosity of about 90%, a thickness of about 3 µm, a bubble point of about 450 KPa, a matrix tensile strength of about 350 MPa in the longitudinal direction and about 250 MPa in the transverse direction. This membrane was imbibed with the same fluoroelastomer as described above. The fluoroelastomer was dissolved in Novec HFE7500 (3M, St Paul, Minn., USA) in an about 2.5% concentration. The solution was coated using a mayer bar onto the ePTFE membrane (while being supported by a polypropylene release film) and dried in a convection oven set to about 145° C. for about 30 seconds. After two coating steps, the resulting composite material of ePTFE/fluoroelastomer had a mass per area of about 4 g/m$^2$.

The final leaflet was comprised of about 30% fluoropolymer by weight with a thickness of 25 µm. Each leaflet had 31 layers of the composite.

The encapsulated frame with frame covering defining a strain relief and a reinforcing member was then attached to the leaflet material in a cylindrical or tubular shape in the following manner. The encapsulated frame with strain relief covering and reinforcing member was placed on the release liner-covered tapered mandrel described above, as shown in FIG. 5D.

Figure 5D:
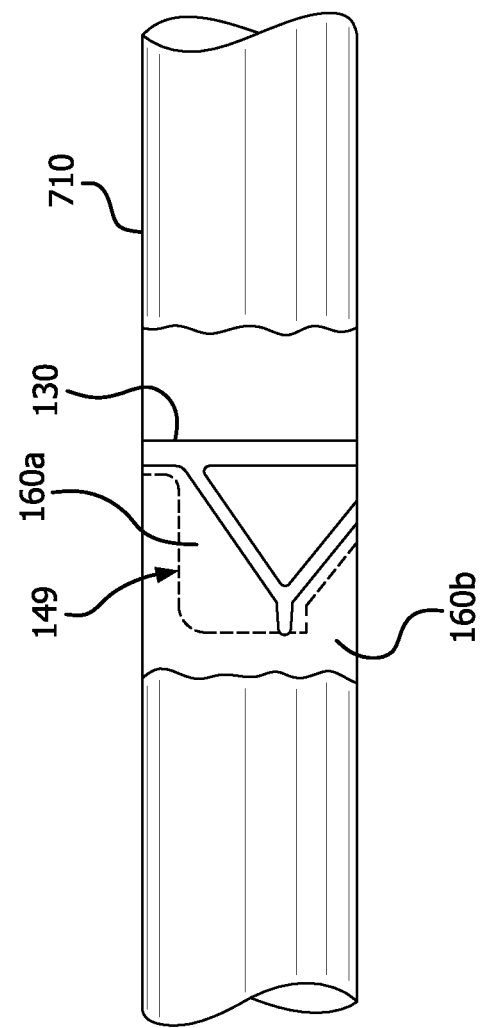
FIG. 5D is a side view of the leaflet frame construct on an assembly mandrel overlaid with leaflet material, in accordance with an embodiment.

Thirty-one layers of the above described leaflet material were circumferentially wrapped over the encapsulated frame, as shown in FIG. 5D.

Approximately ten layers of a sacrificial longitudinally expanded PTFE film having a thickness of about 0.1 mm were tightly wrapped around the covered frame. The resulting assembly was then placed in a convection oven set at 280° C. for 60 minutes. This assembly was removed from the oven and allowed to cool, and the outer sacrificial layers were removed. This assembly was then removed from the mandrel, ensuring that it was released from the inner sacrificial layer.

The leaflet material was trimmed approximately 5 mm above the leaflet frame first end 121a, also referred to as the frame top. The resulting assembly was placed in a convection oven set at 150° C. for 15 min while closing the valve with 5 cm of Hg vacuum to close the leaflets. The assembly was removed from the oven and allowed to cool. Leaflets were trimmed using scissors to a height of approximately 1-2 mm above the coaptation line.

The average maximum leaflet thickness in the leaflet first side region was 281 micrometers and the average maximum leaflet thickness in the leaflet second side region was 27 micrometers. These measurements were an average of three measurements obtained on a Mitutoyo Litematic VL-50A (Aurora, Ill.) digimatic measuring unit.

The performance of the valve leaflets was characterized on a real-time pulse duplicator. The following results were obtained: EOA=1.9 cm$^2$ and regurgitant fraction=2.5%.

A geometric orifice area (GOA) test was performed. With a flow of 450 ml/s of 37° C. saline flowing through the 22 mm ID valve, a picture was taken of the leaflets in the fully open position. This image was analyzed by pasting the image in CAD software (SOLIDWORKS 2012). A circle was drawn connecting the inner surface of the centers of each of the three posts. From the middle of each of these three posts, a diameter line was drawn. These diameter lines split the image into six (6) slices, or two slices per leaflet, similar to FIG. 1C. A spline line 156 was then drawn around the full circumference of the edge of the open leaflets. The geometric orifice area (GOA) for each of the three leaflets was then calculated by calculating the luminal area within the spline for the ⅓ of the total valve area encompassed by each leaflet. This resulted in a calculation of GOA for each leaflet (the sum of these three GOAs equals the GOA of the entire valve). Subsequently, the GOA of each side of the leaflet was calculated by using the diameter line drawn previously which bisects the leaflet. The GOA from the reinforced section of the leaflet is always less than the GOA of the unreinforced section. For the example presented above, the ratio of the GOA on the reinforced side of the leaflet to the total leaflet GOA was 34%, 37%, and 33%, while the other side of the leaflet had a ratio of 66%, 63%, and 67%, respectively.

Test Methods

Pulsatile Flow Testing

The flow performance was characterized by the following process:

The valve assembly was placed within a silicone annular ring (support structure), supporting its outer diameter without changing its diameter, to allow the valve assembly to be subsequently evaluated in a real-time pulse duplicator. The process was performed according to the recommendations of the pulse duplicator manufacturer (ViVitro Laboratories Inc., Victoria BC, Canada).

The valve assembly was then placed into a real-time left heart flow pulse duplicator system. The flow pulse duplicator system included the following components supplied by ViVitro Laboratories Inc., Victoria BC, Canada: a Super Pump, Servo Power Amplifier Part Number SPA 3891; a Super Pump Head, Part Number SPH 5891 B, 38 cm$^2$ cylinder area; a valve station/fixture; Vivitro software capable of waveform control and data collection; I/O module Part Number XXXX, TriPack Part Number TP 2001; a Sensor Interface, Part Number VB 2004; a Sensor Amplifier Component, Part Number AM 9991; and a Square Wave Electro Magnetic Flow Meter (positioned approximately 2 cm upstream of the valve), Carolina Medical Electronics Inc., East Bend, N.C., USA. The outflow chamber used to evaluate the performance of the pulmonary valve was chosen such that the internal diameter of the outflow chamber was matched to that of the valve diameter. A 40 ml source compliance, a large peripheral compliance was added to the tester to simulate physiological pulmonary conditions. Additionally, as a straight outflow chamber was used, the root compliance was not used in the test set-up.

In general, the flow pulse duplicator system uses a fixed displacement, piston pump to produce a desired fluid flow through the valve under test. Testing and definitions are consistent with ISO 5840-3, 2013 except where otherwise noted for testing to pulmonary conditions. While this testing is conducted to pulmonary conditions, testing and use (e.g. aortic, mitral, tricuspid, venous, etc) in other conditions is not excluded.

The heart flow pulse duplicator system was adjusted to produce the desired flow (5.0±0.5 L/min), mean pressure (20±2 mmHg), simulated pulse rate (70 bpm), a 35% systolic duration sinusoidal waveform, and a stroke volume (i.e., the amount of fluid pushed by the driving pump) of 84±1 ml. The operating temperature was 37±1° C. using 0.9% saline as test solution. The valve under test was then cycled for between 5 to 15 minutes.

Pressure and flow data were measured and collected during the test period for ten (10) continuous cardiac cycles, including right ventricular pressures, pulmonary pressures, flow rates, and pump piston position. Parameters used to characterize the valve are effective orifice area and regurgitant fraction. The effective orifice area (EOA), which can be calculated as follows: $EOA(cm^2) = Q_{rms}/(51.6*(\Delta P)^{1/2})$ where $Q_{rms}$ is the root mean square of the flow rate (cm$^3$/s) during the positive pressure interval of systolic period and $\Delta P$ is the mean differential pressure during the positive pressure interval of the systolic period (mmHg) (note that density of saline is taken to be 1 g/cm$^3$, therefore this equation eliminates the density as compared to the equation presented in ISO 5840).

During this test, during the period when the maximum flow is flowing through the valve, a digital picture was taken. This picture was taken from the outflow region with the lens normal to the direction of flow with a field of view to encompass the full outflow side of the valve. The flow rate was recorded from the Pulse Duplicator at this time and the image used for GOA (Geometric Orifice Area) calculations.

Another measure of the hydrodynamic performance of a valve is the regurgitant fraction, which is the amount of fluid or blood regurgitated through the valve divided by the Forward Volume (i.e., amount of flow passing through the valve during the forward phase of the valve).

Steady Flow Testing

To demonstrate the asymmetrical opening of the leaflets in a steady flow apparatus, saline heated to 37° C. was pumped at a steady rate though the valve to open it. Saline was pumped using a pump (WEG Electric, Duluth, Ga., part number 10086261) with voltage regulator (Staco Energy Products, Miamisburg, Ohio, part number 3PN2210B) though the valve at 5 L/min (as measured by a large graduated cylinder and stopwatch). The valve was placed within a silicone holder in the recirculating loop that started and finished within an open 37±1° C. heated reservoir. An image of the valve was taken using a digital camera (Vision Research, Wayne, N.J., Model Miro EX4), and the GOA measured using the same technique as noted previously. For all three leaflets, the geometric open area on one half of each leaflet was 39% of each leaflets total GOA (i.e. other half of leaflet geometric open area was 61% of each leaflets total GOA).

Material Characterization Testing

As used in this application, the surface area per unit mass, expressed in units of m$^2$/g, was measured using the Brunauer-Emmett-Teller (BET) method on a Coulter SA3100 Gas Adsorption Analyzer, Beckman Coulter Inc. Fullerton Calif., USA. To perform the measurement, a sample was cut from the center of the expanded fluoropolymer membrane and placed into a small sample tube. The mass of the sample was approximately 0.1 to 0.2 g. The tube was placed into the Coulter SA-Prep Surface Area Outgasser (Model SA-Prep, P/n 5102014) from Beckman Coulter, Fullerton Calif., USA and purged at about 110° C. for about two hours with helium. The sample tube was then removed from the SA-Prep Outgasser and weighed. The sample tube was then placed into the SA3100 Gas adsorption Analyzer and the BET surface area analysis was run in accordance with the instrument instructions using helium to calculate the free space and nitrogen as the adsorbate gas.

Bubble point and mean flow pore size were measured according to the general teachings of ASTM F31 6-03 using a capillary flow Porometer, Model CFP 1500AEXL from Porous Materials, Inc., Ithaca N.Y., USA. The sample membrane was placed into the sample chamber and wet with SilWick Silicone Fluid (available from Porous Materials Inc.) having a surface tension of about 20.1 dynes/cm. The bottom clamp of the sample chamber had an about 2.54 cm diameter hole. Isopropyl alcohol was used as the test fluid. Using the Capwin software version 7.73.012 the following parameters were set as specified in the table below. As used herein, mean flow pore size and pore size are used interchangeably.

| Parameter | Set Point |
| --- | --- |
| Maxflow (cm$^3$/m) | 200000 |
| Bublflow (cm$^3$/m) | 100 |
| F/PT (old bubltime) | 50 |
| Minbpress (PSI) | 0 |
| Zerotime (sec) | 1 |
| V2incr (cts) | 10 |
| Preginc (cts) | 1 |
| Pulse delay(sec) | 2 |

| Parameter | Set Point |
| --- | --- |
| Maxpre (PSI) | 500 |
| Pulse width (sec) | 0.2 |
| Mineqtime (sec) | 30 |
| Presslew (cts) | 10 |
| Flowslew (cts) | 50 |
| Eqiter | 3 |
| Aveiter | 20 |
| Maxpdif (PSI) | 0.1 |
| Maxfdif (PSI) | 50 |
| Sartp (PSI) | 1 |
| Sartf (cm$^3$/m) | 500 |

Membrane thickness was measured by placing the membrane between the two plates of a Käfer FZ1000/30 thickness snap gauge Käfer Messuhrenfabrik GmbH, Villingen-Schwenningen, Germany. The average of the three measurements was reported.

The presence of elastomer within the pores can be determined by several methods known to those having ordinary skill in the art, such as surface and/or cross section visual, or other analyses. These analyses can be performed prior to and after the removal of elastomer from the leaflet.

Membrane samples were die cut to form rectangular sections about 2.54 cm by about 15.24 cm to measure the weight (using a Mettler-Toledo analytical balance model AG204) and thickness (using a Käfer Fz1000/30 snap gauge). Using these data, density was calculated with the following formula: $\rho = m/w*l*t$, in which: $\rho$=density (g/cm$^3$): m=mass (g), w=width (cm), l=length (cm), and t=thickness (cm. The average of three measurements was reported.

Tensile break load was measured using an INSTRON 122 tensile test machine equipped with flat-faced grips and a 0.445 kN load cell. The gauge length was about 5.08 cm and the cross-head speed was about 50.8 cm/min. The sample dimensions were about 2.54 cm by about 15.24 cm. For longitudinal measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness measured using the Käfer FZ1000/30 snap gauge. The samples were then tested individually on the tensile tester. Three different sections of each sample were measured. The average of the three maximum loads (i.e., peak force) measurements was reported. The longitudinal and transverse matrix tensile strengths (MTS) were calculated using the following equation: MTS=(maximum load/cross-section area)*(bulk density of PTFE)/(density of the porous membrane), wherein the bulk density of the PTFE was taken to be about 2.2 g/cm$^3$. Bending stiffness was measured by following the general procedures set forth in ASTM D790. Unless large test specimens are available, the test specimen must be scaled down. The test conditions were as follows. The leaflet specimens were measured on a three-point bending test apparatus employing sharp posts placed horizontally about 5.08 mm from one another. An about 1.34 mm diameter steel bar weighing about 80 mg was used to cause deflection in the y (downward) direction, and the specimens were not restrained in the x direction. The steel bar was slowly placed on the center point of the membrane specimen. After waiting about 5 minutes, the y deflection was measured. Deflection of elastic beams supported as above can be represented by: $d = F*L^3/48*EI$, where F (in Newtons) is the load applied at the center of the beam length, L (meters), so L=½ distance between suspending posts, and EI is the bending stiffness (Nm). From this relationship the value of EI can be calculated. For a rectangular cross-section: $I = t^3*w/12$, where I=cross-sectional moment of inertia, t=specimen thickness (meters), w=specimen width (meters). With this relationship, the average modulus of elasticity over the measured range of bending deflection can be calculated.

It will be apparent to those skilled in the art that various modifications and variations can be made in the present embodiments without departing from the spirit or scope of the embodiments. Thus, it is intended that the present embodiments cover the modifications and variations of this invention provided they come within the scope of the appended claims and their equivalents.

What is claimed:

1. A prosthetic valve comprising:
a plurality of leaflets, each leaflet including a leaflet first side region and a leaflet second side region opposite from the leaflet first side region, the leaflet first side region having a first bending stiffness that is greater than a second bending stiffness of the second side region, wherein each leaflet opens asymmetrically, wherein the leaflet second side region is operable to initiate opening before the leaflet first side region and where the leaflet first side region is operable to initiate closing before the leaflet second side region, the leaflet first side region of a first leaflet being coupled to a leaflet second side region of an adjacent leaflet.

2. The prosthetic valve of claim 1, wherein the leaflets define an orifice, wherein each of the leaflet first side regions extend further into the orifice than each of the leaflet second side regions when the leaflets are in an open position.

3. The prosthetic valve of claim 1, wherein each leaflet includes the leaflet first side region being defined by a leaflet first side, each leaflet includes the leaflet second side region being defined by the leaflet second side.

4. The prosthetic valve of claim 1, further comprising a leaflet frame forming a plurality of leaflet windows supporting a corresponding one of the leaflets, each window and corresponding leaflet defining an orifice for fluid flow when the leaflet is in an open position, wherein when in the open position, the leaflet first side region contributes to a smaller geometric orifice area as compared with the leaflet second side region.

5. The prosthetic valve of claim 4, wherein the leaflet second side region opens further than the leaflet first side region during forward flow of a fluid through the orifice at a flow rate of 350 ml/sec.

6. The prosthetic valve of claim 4 wherein when in the open position, the leaflet first side region contributes up to a 70 percent smaller geometric orifice area as compared with the leaflet second side region.

7. The prosthetic valve of claim 1, wherein the leaflet comprises at least one layer of a composite material, at least a first portion of the first side region comprises more layers of composite material than the second side region.

8. The prosthetic valve of claim 7, wherein the first portion of the leaflet first side region has a first thickness that is up to ten times more than a second thickness of the leaflet second side region.

9. The prosthetic valve of claim 7, wherein a first thickness of the leaflet first side region is at least 280 micrometer and the leaflet second side region has a second thickness of 25 micrometer or greater.

10. The prosthetic valve of claim 7 wherein at least the first portion of the leaflet first side region further comprises a leaflet reinforcing member, the leaflet reinforcing member being operable to provide the first portion of the leaflet first side region with the first bending stiffness that is greater than the second bending stiffness of the leaflet second side region.

11. The prosthetic valve of claim 10, wherein the leaflet reinforcing member comprises at least one layer of composite material coupled to at least the first portion of the leaflet first side region.

12. The prosthetic valve of claim 1, wherein a first thickness of the leaflet first side region is greater than 110% of a second thickness of the leaflet second side region.

13. The prosthetic valve of claim 1, wherein the leaflet comprises a polymeric material.

14. The prosthetic valve of claim 1, further comprising:
a leaflet frame having a generally tubular shape, the leaflet frame defining a plurality of leaflet windows wherein each of the leaflet windows includes a leaflet window first side, a leaflet window second side opposite the leaflet window first side, a leaflet window base therebetween, wherein a leaflet window side of one leaflet window is interconnected with a leaflet window side of an adjacent leaflet window,
wherein the plurality of leaflets being coupled to the leaflet frame, each leaflet including a free edge, a base opposite from the free edge and coupled to the leaflet window base, and a leaflet central region between the leaflet first side region and the leaflet second side region, the leaflet first side region being coupled to the leaflet window first side and the leaflet second side region being coupled to the leaflet window second side.

15. The prosthetic valve of claim 14, wherein two adjacent leaflet window first side and leaflet window second side terminate at a commissure post.

16. The prosthetic valve of claim 1, further comprising a leaflet frame having a generally tubular shape, the leaflet frame defining a plurality of leaflet windows wherein each of the leaflet windows includes a leaflet window first side, a leaflet window second side opposite the leaflet window first side, a leaflet window base therebetween, wherein each leaflet includes a free edge, a base opposite from the free edge and coupled to the leaflet window base, wherein the leaflet reinforcing member extends to the free edge of the leaflet.

17. The prosthetic valve of claim 16, wherein two adjacent leaflet window first side and leaflet window second side terminates at a commissure post, the leaflet first side region being coupled to the leaflet window first side, the leaflet second side region being coupled to the leaflet window second side.

18. The prosthetic valve of claim 17, further comprising a vertical element extending from each of the commissure posts.

19. The prosthetic valve of claim 1, further comprising:
a leaflet frame having a generally tubular shape, the leaflet frame defining a plurality of leaflet windows wherein each of the leaflet windows includes a leaflet window first side and a leaflet window second side opposite the leaflet window first side and coupled thereto, wherein a leaflet window side of one leaflet window is interconnected with a leaflet window side of an adjacent leaflet window; and
a leaflet reinforcing member coupled to the leaflet window first side,
wherein the plurality of leaflets are coupled to the leaflet frame, each leaflet including a free edge extending across the leaflet window first side and the leaflet window second side of a corresponding one of the plurality of leaflet windows, wherein the leaflet first side region is coupled to the leaflet reinforcing member making the leaflet first side region stiffer than the leaflet second side region.

20. The prosthetic valve of claim 19, wherein the plurality of windows of the leaflet frame include three interconnected leaflet windows each having a trapezoidal shape.

21. The prosthetic valve of claim 20, wherein the leaflet comprises a laminate.

22. The prosthetic valve of claim 21, wherein the laminate has more than one layer of a fluoropolymer membrane.

23. The prosthetic valve of claim 22, wherein the fluoropolymer membrane comprises ePTFE.

24. The prosthetic valve of claim 20, wherein the leaflet comprises a film having at least one fluoropolymer membrane having a plurality of pores and an elastomer present in the plurality of pores of the at least one fluoropolymer membrane.

25. The prosthetic valve of claim 24, wherein the film comprises less than about 80% fluoropolymer membrane by weight.

26. The prosthetic valve of claim 24, wherein the elastomer comprises (per)fluoroalkylvinylethers (PAVE).

27. The prosthetic valve of claim 24, wherein the elastomer comprises a copolymer of tetrafluoroethylene and perfluoromethyl vinyl ether.

28. The prosthetic valve of claim 1, wherein the leaflet comprises a polymeric material.

* * * * *